(12) United States Patent
Muraoka et al.

(10) Patent No.: US 9,064,302 B2
(45) Date of Patent: Jun. 23, 2015

(54) DIAGNOSIS ASSISTANCE SYSTEM AND COMPUTER READABLE STORAGE MEDIUM

(75) Inventors: Shintaro Muraoka, Hachioji (JP); Syou Noji, Tachikawa (JP); Tetsuo Shimada, Hino (JP)

(73) Assignee: KONICA MINOLTA, INC. (JP)

( * ) Notice: Subject to any disclaimer, the term of this patent is extended or adjusted under 35 U.S.C. 154(b) by 164 days.

(21) Appl. No.: 13/819,222

(22) PCT Filed: Mar. 9, 2011

(86) PCT No.: PCT/JP2011/055518
§ 371 (c)(1),
(2), (4) Date: Feb. 26, 2013

(87) PCT Pub. No.: WO2012/026145
PCT Pub. Date: Mar. 1, 2012

(65) Prior Publication Data
US 2013/0156267 A1 Jun. 20, 2013

(30) Foreign Application Priority Data
Aug. 27, 2010 (JP) ................................. 2010-190240

(51) Int. Cl.
*G06K 9/00* (2006.01)
*G06T 7/00* (2006.01)
*A61B 6/00* (2006.01)
(Continued)

(52) U.S. Cl.
CPC ............... *G06T 7/0012* (2013.01); *A61B 5/026* (2013.01); *A61B 5/087* (2013.01); *A61B 6/5217* (2013.01); *G06T 7/0016* (2013.01); *G06T 2200/24* (2013.01); *G06T 2207/30061* (2013.01); *G06K 9/3241* (2013.01); *A61B 6/463* (2013.01); *A61B 6/469* (2013.01); *G06T 2207/10016* (2013.01); *G06T 2207/10116* (2013.01);
(Continued)

(58) Field of Classification Search
None
See application file for complete search history.

(56) References Cited

U.S. PATENT DOCUMENTS 8,229,193 B2 * 7/2012 Novatzky et al. ............. 382/128
2004/0167389 A1 * 8/2004 Brabrand ...................... 600/407
(Continued)

FOREIGN PATENT DOCUMENTS

JP 8110939 A 4/1996
JP 2004-312434 A 11/2004
(Continued)

OTHER PUBLICATIONS

Notification of Refusal for Japanese Application No. 2012-530549, dispatched Oct. 14, 2014, with English translation.
(Continued)

*Primary Examiner* — Shervin Nakhjavan
(74) *Attorney, Agent, or Firm* — Cantor Colburn LLP

(57) ABSTRACT

Provided is a diagnosis assistance system. The system includes, an imaging unit, an analysis unit, an operation unit, and a display unit. The analysis unit extracts a subject region from each of the plurality of image frames generated by the imaging unit, divides the extracted subject region into a plurality of regions, and analyzes the divided regions correlated among the plurality of image frames, thereby calculating a predetermined feature quantity indicating motions of the divided regions. The operation unit allows a user to select a region serving as a display target of an analysis result by the analysis unit. The display unit displays the calculated feature quantity regarding the selected region.

7 Claims, 21 Drawing Sheets

(51) Int. Cl.
*G06K 9/32* (2006.01)
*A61B 5/026* (2006.01)
*A61B 5/087* (2006.01)

(52) U.S. Cl.
CPC ............... *G06T 2207/20021* (2013.01); *G06T 2207/30104* (2013.01); *A61B 6/507* (2013.01)

(56) References Cited

U.S. PATENT DOCUMENTS

| | | | |
|---|---|---|---|
| 2009/0062651 A1* | 3/2009 | Chomas et al. | 600/443 |
| 2010/0054556 A1* | 3/2010 | Novatzky et al. | 382/128 |
| 2010/0246925 A1* | 9/2010 | Nagatsuka et al. | 382/132 |
| 2011/0040168 A1* | 2/2011 | Arnaud et al. | 600/407 |
| 2011/0144495 A1* | 6/2011 | Wilkening et al. | 600/443 |

FOREIGN PATENT DOCUMENTS

| | | |
|---|---|---|
| JP | 2007-275196 A | 10/2007 |
| JP | 2007275196 A | 10/2007 |
| JP | 2009-153677 A | 7/2009 |
| JP | 2009153677 A | 7/2009 |
| JP | 2009-273671 A | 11/2009 |
| JP | 2009273671 A | 11/2009 |
| WO | 2006/137294 A1 | 12/2006 |
| WO | 2009078297 A1 | 6/2009 |

OTHER PUBLICATIONS

Notification of the First Office Action for corresponding Chinese Application No. or Patent No. 201180041370.4; Date of Issuance, Oct. 10, 2014; with English Translation.

International Search Report for International application No. PCT/JP2011/055518, mailed May 17, 2011, with English translation.

International Preliminary Report on Patentability and Written Opinion for International Application No. PCT/JP2011/055518; Date of Issuance: Mar. 19, 2013 with English Translation.

* cited by examiner

US 9,064,302 B2

DIAGNOSIS ASSISTANCE SYSTEM AND COMPUTER READABLE STORAGE MEDIUM

CROSS REFERENCE TO RELATED APPLICATIONS

This is a U.S. National Stage of Application No. PCT/JP2011/055518, filed on 9 Mar. 2011. Priority under 35 U.S.C. §119(a) and 35 U.S.C. §365(b) is claimed from Japanese Application No. 2010-190240, filed 27 Aug. 2010, the disclosure of which is also incorporated herein by reference.

TECHNICAL FIELD

The present invention relates to a diagnosis assistance system and program.

BACKGROUND ART

Heretofore, a physician has comprehensively carried out a diagnosis about a ventilatory function of lungs by both pieces of information coming from an eye and an ear, such as image information by a chest X-ray film (an image imaged when a lung field becomes maximum at the time of deep breathing) and sound information of a stethoscope.

As opposed to this, in recent years, an attempt has been being made, which is to image a dynamic image of a chest portion by using a semiconductor image sensor such as an FPD (flat panel detector), and to apply the dynamic image to the diagnosis. For example, in Patent Literature 1, there is described a technology for generating difference images showing differences of signal values among a plurality of image frames which compose the dynamic image, and obtaining maximum values of the respective signal values from the generated difference images to display the obtained image.

PRIOR ART DOCUMENT

Patent Document

Patent Document 1: Japanese Patent Laid-Open Publication No. 2004-312434

DISCLOSURE OF THE INVENTION

Problems to be Solved by the Invention

However, under the present circumstances, the diagnosis by the sound (ear) of the stethoscope depends on a proficiency level of each physician since it is difficult to make propagation of diagnosability at a conference and the like which is based on a teaching image like the chest X-ray film, and to simultaneously confirm the diagnosis by a plurality of physicians like the chest X-ray film concerned. Moreover, when a patient meets the physician while interposing the stethoscope therebetween, the lungs sometimes exhibit behavior different from that at a normal time owing to tension of the patient, and proficiency also including a determination for an influence of this is required.

Meanwhile, in the technology of Patent Literature 1, simply the maximum values of such inter-frame difference values for each of pixels of the dynamic image are calculated and the obtained image is displayed, and it is difficult for a physician other than a proficient pulmonologist to grasp a state of a disease only from such result.

It is an object of the present invention to provide a GUI-containing system that effectively utilizes an image imaged dynamically, integrates information for use in the diagnosis into a visual series, and enables even a physician, who has little experience with the stethoscope, to carry out accurate diagnosis.

Means for Solving the Problem

In order to solve the above-described problems, in accordance with a first aspect of the present invention, there is provided a diagnosis assistance system including:

an imaging unit which performs dynamic imaging for a subject and which generates a plurality of successive image frames;

an analysis unit which extracts a subject region from each of the plurality of generated image frames, which divides the extracted subject region into a plurality of regions, and which analyzes the divided regions correlated among the plurality of image frames, thereby calculating a predetermined feature quantity indicating motions of the divided regions;

an operation unit which allows a user to select a region serving as a display target of an analysis result by the analysis unit from among the divided regions; and a display unit which displays the feature quantity regarding the region selected by the operation unit, the feature quantity being calculated by the analysis unit.

Preferably, the analysis unit further calculates a predetermined feature quantity indicating a motion of a whole of the subject region, and the display unit simultaneously displays the feature quantity indicating a motion of the region selected by the operation unit, the motion being calculated by the analysis unit, and the feature quantity indicating the motion of the whole of the subject region.

Preferably, the analysis unit calculates one or a plurality of the feature quantities indicating the motion of the divided region.

Preferably, the display unit displays one image frame from among the plurality of generated image frames, and the operation unit is configured to be capable of selecting one or a plurality of regions from the image frame displayed on the display unit, the region serving as a display target of the analysis result.

Preferably, the display unit displays the plurality of generated image frames in a format of a moving image, and the operation unit is configured to be capable of selecting one or a plurality of regions from the moving image displayed on the display unit, the region serving as a display target of the analysis result.

Preferably, the display unit further displays one image frame from among the plurality of generated image frames, and displays the respective divided regions of the one image frame by a color corresponding to a value of the feature quantity calculated by the analysis unit.

Preferably, the analysis unit calculates an average value of pixel signal values in the divided region of the plurality of image frames, and calculates a time change of a calculated average signal value as a feature quantity indicating a motion of the region, and the display unit displays, as a waveform, the time change of the average signal value of the region selected by the operation unit, the time change being calculated by the analysis unit.

Preferably, the imaging unit is a unit for imaging a dynamic image of a chest portion, and in a case where one region of lung field regions is selected by the operation unit, the display unit displays a feature quantity of a region of other lung field that is body axis-symmetric to the selected region simultaneously with a feature quantity of the selected region.

Preferably, the feature quantity to be calculated by the analysis unit is configured to be selectable in advance from among the plurality of feature quantities by the operation unit.

Preferably, the feature quantity indicating the motion of the divided region is a feature quantity indicating ventilation or blood flow of the region.

In accordance with a second aspect of the present invention, preferably, a program allows a computer to function as:

an analysis unit which extracts a subject region from each of a plurality of image frames showing movement of a subject, which divides the extracted subject region into a plurality of regions, and which analyzes the divided regions correlated among the plurality of image frames, thereby calculating a predetermined feature quantity indicating motions of the divided regions;

an operation unit which allows a user to select a region serving as a display target of an analysis result by the analysis unit from among the divided regions; and a display unit which displays the feature quantity regarding the region selected by the operation unit, the feature quantity being calculated by the analysis unit.

Advantageous Effect of the Invention

In accordance with the present invention, it is made possible to provide the GUI-containing system that effectively utilizes the image imaged dynamically, integrates the information for use in the diagnosis into the visual series, and enables even the physician, who has little experience with the stethoscope, to carry out the accurate diagnosis.

EMBODIMENT FOR CARRYING OUT THE INVENTION

A description is made below in detail of embodiments of the present invention with reference to the drawings. However, the scope of the invention is not limited to the illustrated examples.

<First Embodiment>

[Configuration of Diagnosis Assistance System 100]

First, a description is made of a configuration.

Figure 1:
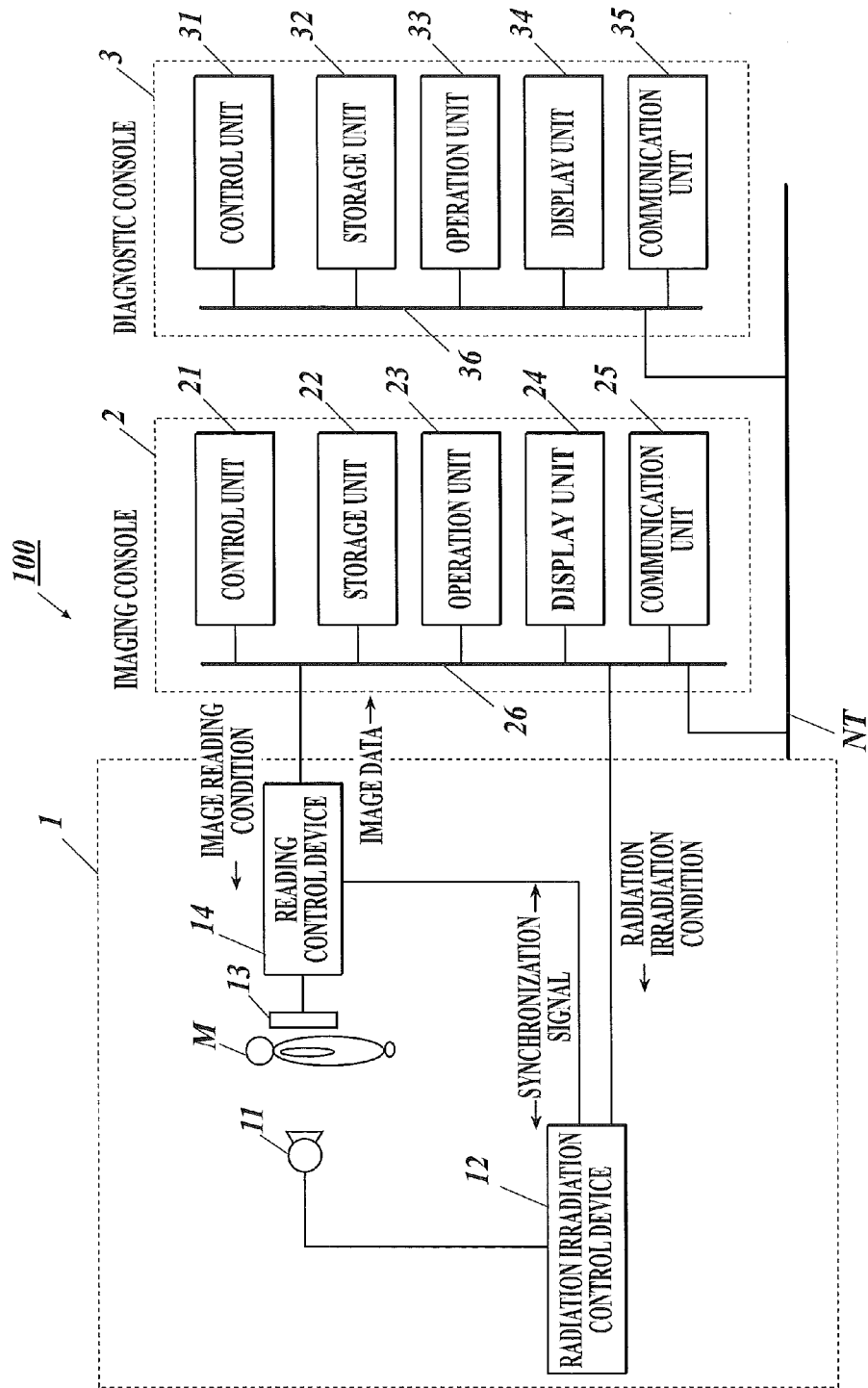
FIG. 1 is a view showing an overall configuration of a diagnosis assistance system in an embodiment of the present invention.

FIG. 1 shows an overall configuration of a diagnosis assistance system 100 in this embodiment.

As shown in FIG. 1, the diagnosis assistance system 100 is configured in such a manner that an imaging apparatus 1 and an imaging console 2 are connected to each other through a communication cable and the like, and that the imaging console 2 and a diagnostic console 3 are connected to each other through a communication network NT such as a LAN (Local Area Network) and the like. The respective apparatuses which configure the diagnosis assistance system 100 conform to the DICOM (Digital Images and Communications in Medicine) standard, and communication among the respective apparatuses is performed in accordance with DICOM.

[Configuration of Imaging Apparatus 1]

For example, the imaging apparatus 1 is an apparatus that images movements of a chest portion, which have cycles such as morphological changes of lung expansion and contract which follow breathing movement, and heart beats. Such dynamic imaging is performed by continuously irradiating a radiation such as an X-ray onto a human chest portion in a pulse manner and obtaining (that is, successively imaging) a plurality of images. A series of the images obtained by such successive imaging is called dynamic images. Moreover, each of the plurality of images which compose the dynamic images is called an image frame.

As shown in FIG. 1, the imaging apparatus 1 is composed of a radiation generation device 11, a radiation irradiation control device 12, a radiation detection unit 13, a reading control device 14 and the like.

Figure 2:
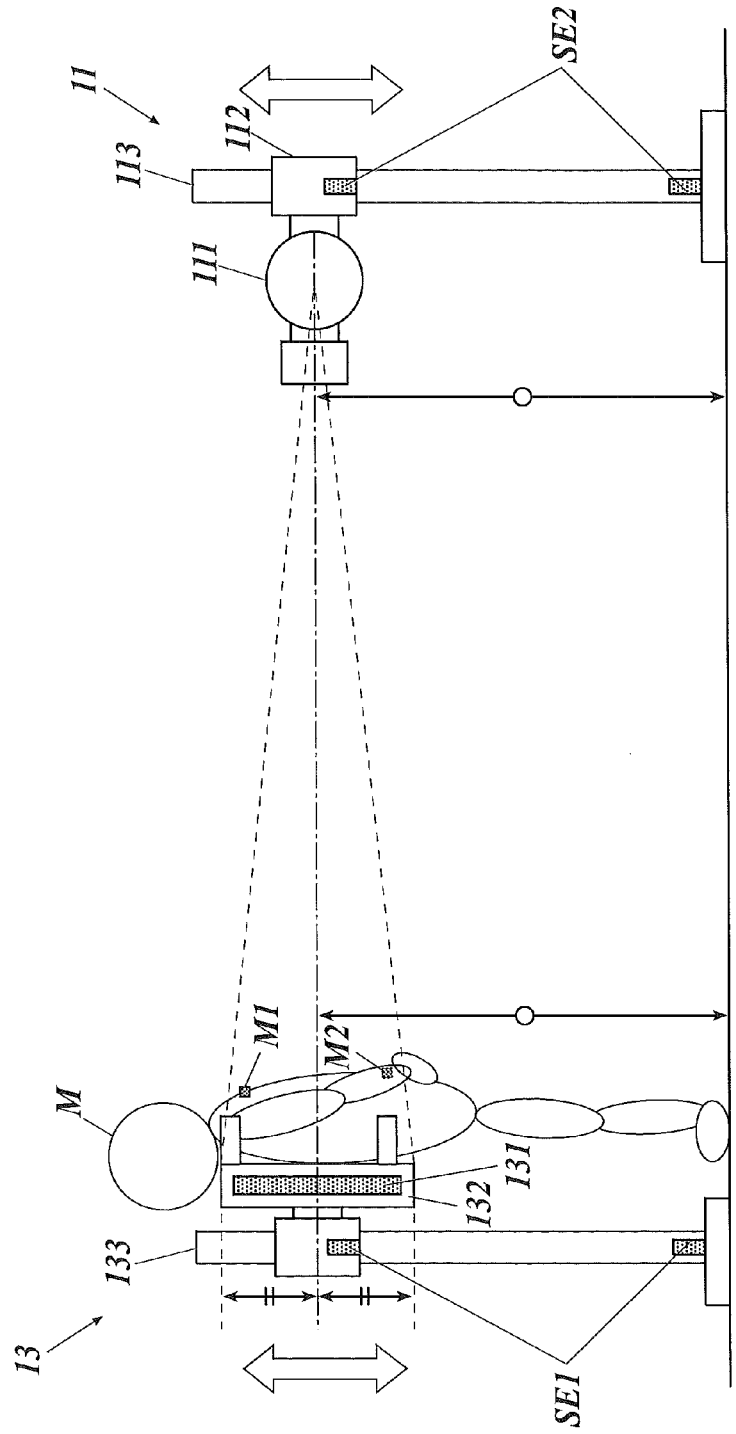
FIG. 2 is a view showing a detailed configuration example of a radiation generation apparatus and a radiation detection unit in FIG. 1.

As shown in FIG. 2, the radiation generation device 11 is composed by including a radiation source 111, a radiation source holding portion 112, a support base shaft 113 and the like.

The radiation source 111 is arranged at a position opposite to a radiation detector 131 while sandwiching a subject M therebetween, and irradiates a radiation (X-ray) onto the subject M in accordance with control of the radiation irradiation control device 12. The radiation source 111 is held by the radiation source holding portion 112 so as to be capable of ascending and descending along the support base shaft 113, and at a time of the imaging, is adjusted by a drive mechanism not shown based on control from the radiation irradiation control device 12 so that a height (distance) from a floor to a focus position of the radiation source 111 can become the same as a height from the floor to a center of the radiation detector 131. It is preferable that a distance between the radiation source 111 and the radiation detector 131 be 2 m or more.

The radiation irradiation control device 12 is connected to the imaging console 2, and controls the radiation generation device 11 to perform the radiation imaging based on radiation irradiation conditions inputted from the imaging console 2. The radiation irradiation conditions inputted from the imaging console 2 are, for example, a pulse rate, a pulse width, a pulse interval, timing of starting/ending the imaging, a value of an X-ray tube current, a value of an X-ray tube voltage, a filter type and the like at a time of the continuous irradiation. The pulse rate is the number of irradiation times per second, and coincides with a frame rate to be described later. The pulse width is a radiation irradiation time per radiation irradiation. The pulse interval is a time from a start of one radiation irradiation to a start of next radiation irradiation in the successive imaging, and coincides with a frame interval to be described later.

Moreover, the radiation irradiation control device 12 controls the respective units of the radiation generation device 11 so that the height from the floor to the focus position of the radiation source 111 can become the same as the height from the floor to the center of the radiation detector 131, which is to be outputted from the reading control device 14.

As shown in FIG. 2, the radiation detection unit 13 is composed by including the radiation detector 131, a detector holding portion 132, a support base shaft 133 and the like.

The radiation detector 131 is composed of a semiconductor image sensor such as an FPD. For example, the FPD has a glass substrate and the like. At a predetermined position on the substrate, a plurality of pixels, which detect the radiation irradiated from the radiation source 111 and having transmitted at least through the subject M in response to an intensity of the radiation concerned and convert the detected radiation into electrical signals, followed by accumulation thereof, are arrayed in a matrix fashion. For example, the respective pixels are composed of switching units such as TFTs (Thin Film Transistors).

As shown in FIG. 2, the radiation detector 131 is held by the detector holding portion 132 so as to be capable of ascending and descending along the support base shaft 133, and at the time of the imaging, is capable of adjusting a position (height from a floor surface) of the detector holding portion 132 by an operation for a foot switch (not shown) or the like by a radiographer according to a height of the subject M.

The reading control device 14 is connected to the imaging console 2. The reading control device 14 controls the switching units of the respective pixels of the radiation detector 131 based on image reading conditions inputted from the imaging console 2, sequentially switches reading of the electrical signals accumulated in the respective pixels concerned, and reads the electrical signals accumulated in the radiation detector 131, thereby obtains image data. This image data is the image frame. Then, the reading control device 14 sequentially outputs such obtained image frames to the imaging console 2. For example, the image reading conditions are the frame rate, the frame interval, a pixel size, an image size (matrix size) and the like. The frame rate is the number of image frames to be obtained per second, and coincides with the pulse rate. The frame interval is a time from a start of one obtaining operation for the image frame to a start of a next obtaining operation for the image frame in the successive imaging, and coincides with the pulse interval. Note that, after the imaging of all the image frames is ended, the image frames may be collectively outputted to the imaging console.

Here, the radiation irradiation control device 12 and the reading control device 14 are connected to each other, and at the time of the imaging, transfer synchronizing signals there between, whereby radiation irradiation operations are synchronized with a series of image reading operations with a cycle from resetting through accumulation and data reading to the resetting. Besides, at a time of calibration of obtaining a plurality of dark images in order to calculate an offset correction coefficient for use in an offset correction to be described later, the series of image reading operations with the cycle from the resetting through the accumulation and the data reading to the resetting is performed in a state where the image reading operations concerned are not synchronized with the radiation irradiation operations and the radiation is not irradiated; however, the image reading operations may be performed at either of timing before a series of the dynamic imaging and timing after the series of dynamic imaging. Moreover, height information of the height from the floor to the center of the radiation detector 131 (output value from a range finding sensor SE1) is outputted from the reading control device 14 to the radiation irradiation control device 12, and the height from the floor to the center of the radiation detector 131 and the height from the floor to the focus position of the radiation source 111 are allowed to coincide with each other.

[Configuration of Imaging Console 2]

The imaging console 2 outputs the radiation irradiation conditions and the image reading conditions to the imaging apparatus 1, and controls the radiation imaging and the radiation image reading operations by the imaging apparatus 1, and in addition, displays the dynamic image, which is obtained by the imaging apparatus 1, for the purpose of allowing the radiographer to confirm positioning and to confirm whether or not the dynamic image concerned is an image suitable for the diagnosis (whether or not dynamic images of desired breathing cycles or more have been able to be obtained, whether or not the dynamic images have become images with bad granularity owing to lack of a dose of the radiation irradiation, and so on).

As shown in FIG. 1, the imaging console 2 is composed by including a control unit 21, a storage unit 22, an operation unit 23, a display unit 24, and a communication unit 25, and the respective units are connected to one another by a bus 26.

The control unit 21 is composed of a CPU (Central Processing Unit), a RAM (Random Access Memory) and the like. In response to operations for the operation unit 23, the CPU of the control unit 21 reads out a system program and a variety of processing programs, which are stored in the storage unit 22, expands these programs in the RAM, executes various pieces of processing, which include imaging control processing as described later, in accordance with the expanded programs, and performs centralized control for operations of the respective units of the imaging console 2 and the radiation irradiation operations and reading operations of the imaging apparatus 1.

The storage unit 22 is composed of a non-volatile semiconductor memory, a hard disk or the like. The storage unit 22 stores the variety of programs to be executed in the control unit 21, and parameters necessary to execute the processing by the programs, or data such as processing results. For example, the storage unit 22 stores an imaging control processing program for executing the imaging control processing shown in FIG. 3. Moreover, the storage unit 22 stores the radiation irradiation conditions and the image reading conditions. The variety of programs is stored in a form of readable program codes, and the control unit 21 sequentially executes operations according to the program codes concerned.

The operation unit 23 is composed of: a keyboard including cursor keys, number input keys, various function keys and the like; and a pointing device such as a mouse, and outputs instruction signals, which are inputted by key operations on the keyboard and mouse operations, to the control unit 21. Moreover, the operation unit 23 may include a touch panel on a display screen of the display unit 24, and in this case, outputs instruction signals, which are inputted through the touch panel, to the control unit 21.

The display unit 24 is composed of a monitor such as an LCD (Liquid Crystal Display) and a CRT (Cathode Ray Tube), and displays the input instructions from the operation unit 23, the data and the like in accordance with instructions of display signals inputted from the control unit 21.

The communication unit 25 includes a LAN adapter, a modem, a TA (Terminal Adapter) and the like, and controls data transmission/reception with the respective devices connected to a communication network NT.

[Configuration of Diagnostic Console 3]

The diagnostic console 3 is a dynamic image processing apparatus for obtaining a dynamic image from the imaging console 2, displaying the obtained dynamic image and allowing a physician to perform a reading diagnosis.

As shown in FIG. 1, the diagnostic console 3 is composed by including a control unit 31, a storage unit 32, an operation unit 33, a display unit 34, and a communication unit 35, and the respective units are connected to one another by a bus 36.

The control unit 31 is composed of a CPU, a RAM and the like. In response to operations for the operation unit 33, the CPU of the control unit 31 reads out a system program and a variety of processing programs, which are stored in the storage unit 32, expands these programs in the RAM, executes various pieces of processing, which include image analysis processing as described later, in accordance with the expanded programs, and performs centralized control for operations of the respective units of the diagnostic console 3.

The storage unit 32 is composed of a non-volatile semiconductor memory, a hard disk or the like. The storage unit 32 stores the variety of programs, which include an image analysis processing program for executing the image analysis processing in the control section 31, and parameters necessary to execute the processing by the programs, or data such as processing results. These various programs are stored in a form of readable program codes, and the control unit 31 sequentially executes operations according to the program codes concerned. For example, the storage unit 32 stores setting information of a display mode inputted by the operation unit 33 (that is, setting information of a display mode of an analysis result of the dynamic image).

The operation unit 33 is composed of: a keyboard including cursor keys, number input keys, various function keys and the like; and a pointing device such as a mouse, and outputs instruction signals, which are inputted by key operations for the keyboard and mouse operations, to the control unit 31. Moreover, the operation unit 33 may include a touch panel on a display screen of the display unit 34, and in this case, outputs instruction signals, which are inputted through the touch panel, to the control unit 31.

In this embodiment, the operation unit 33 is composed so as to be capable of setting a display mode of an analysis result in the image analysis processing to be described later. As the display mode, the operation unit 33 is composed so as to be capable of setting for example, (a) as to whether a display target region of the analysis result is to be selected by a user or is to be set to a predetermined region (automatically), (b) as to whether only an analysis result about ventilation is to be displayed or an analysis result about a blood flow is to be displayed together with that about the ventilation, (c) as to whether or not to perform list display for analysis results of the respective sub-regions in a lung field, which are as additional information, on a still image together therewith, (d) as to whether or not to perform moving image display for an analysis result of a waveform, which is as additional information, (d) as to which feature quantity among a plurality of feature quantities is to be used as an analysis target, and the like.

The display unit 34 is composed of a monitor such as an LCD and a CRT, and displays the input instructions from the operation unit 33, the data and the like in accordance with instructions of display signals to be inputted from the control unit 31.

The communication unit 35 includes a LAN adapter, a modem, a TA and the like, and controls data transmission/reception with the respective devices connected to the communication network NT.

[Operations of Diagnosis Assistance System 100]

Next, a description is made of operations in the above-described diagnosis assistance system 100.

(Operations of Imaging Apparatus 1 and Imaging Console 2)

First, a description is made of imaging operations by the imaging apparatus 1 and the imaging console 2.

Figure 3:
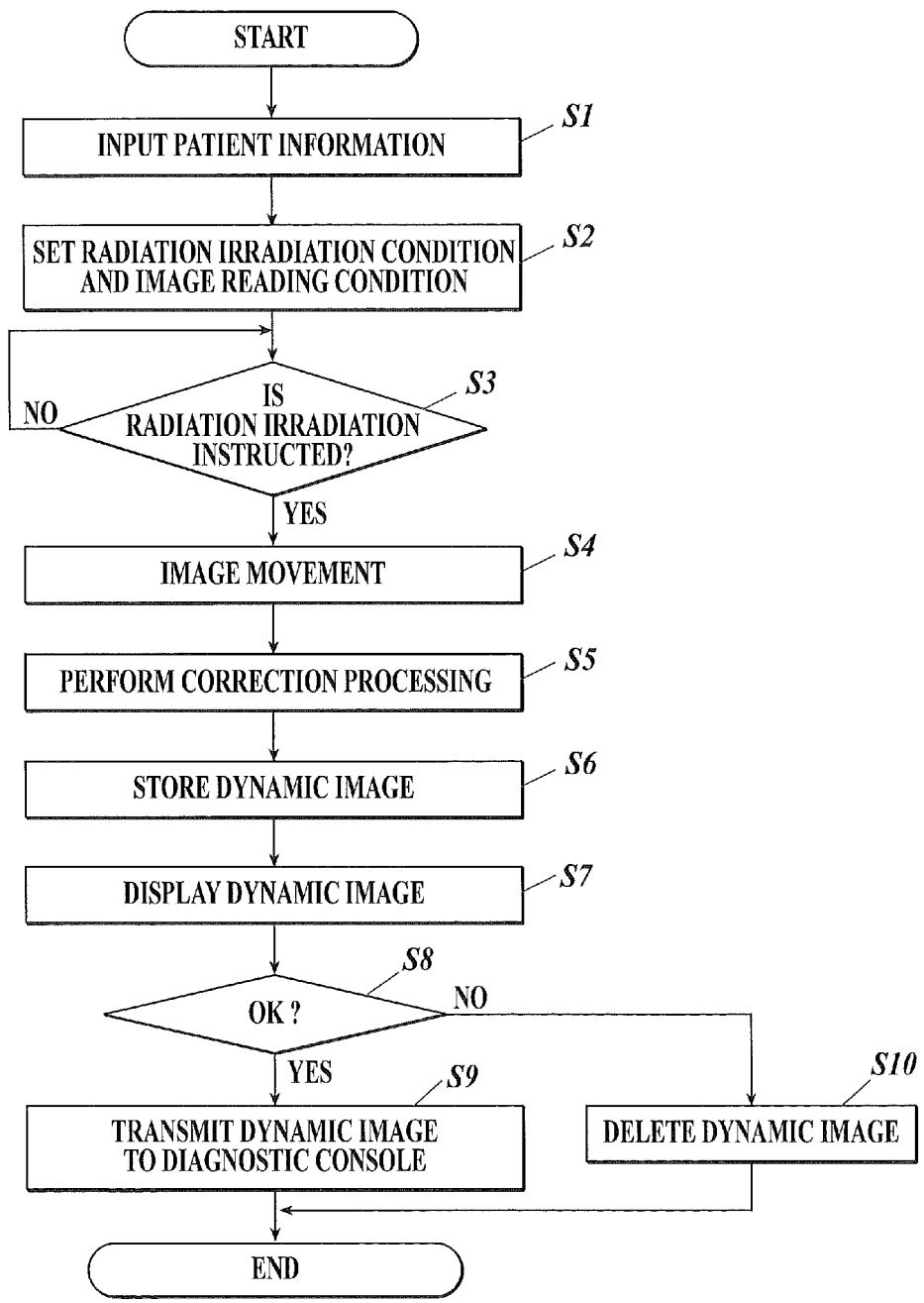
FIG. 3 is a flowchart showing imaging control processing to be executed by a control unit of an imaging console in FIG. 1.

In FIG. 3, the image control processing to be executed in the control unit 21 of the imaging console 2 is shown. The imaging control processing is executed by cooperation between the control unit 21 and the imaging control processing program stored in the storage unit 22.

First, the operation unit 23 of the imaging console 2 is operated by the radiographer, and input of patient information of an imaging target (subject M) (name, stature, weight, age, sex and the like of a patient) is performed (Step S1).

Subsequently, the radiation irradiation conditions are read out from the storage unit 22, and are set in the radiation irradiation control device 12, and in addition, the image reading conditions are read out from the storage unit 22, and are set in the reading control device 14 (Step S2). Here, it is preferable to set the frame rate (pulse rate) at 7.5 frames/second or more in consideration of a human cardiac cycle.

Subsequently, an instruction for the radiation irradiation by the operation for the operation unit 23 is awaited.

The radiographer performs an imaging preparation such as positioning and the like of the patient in the imaging apparatus 1. Specifically, the radiographer adjusts the height of the detector holding portion 132, on which the radiation detector 131 is mounted, by the foot switch (not shown) according to the stature of the subject M (patient). Moreover, the radiographer pastes X-ray opaque markers, which are for correcting a body motion, onto the subject M at two spots or more (here, two spots of a marker M1 and marker M2). Moreover, the radiographer instructs the patient to relax for the purpose of obtaining a dynamic image at the time of resting breathing.

In the imaging apparatus 1, when the height of the detector holding portion 132 is adjusted by the operation of the radiographer, the distance from the floor to the center of the radiation detector 131 is obtained by the range finding sensor SE1, and is outputted to the reading control device 14. In the reading control device 14, an output value of the range finding sensor SE1 is outputted as height information to the radiation irradiation control device 12. In the radiation irradiation control device 12, in order that a value of a distance from the floor to the focus position of the radiation source 111, which is to be outputted from a range finding sensor SE2, can become the same as the value outputted from the reading control device 14, a drive mechanism (not shown) is driven, and a height of the radiation source holding portion 112 is adjusted.

When the positioning of the subject M is ended, the radiographer inputs a radiation irradiation instruction by the operation unit 23 of the imaging console 2.

When the radiation irradiation instruction is inputted by the operation unit 23 (Step S3; YES), an imaging start instruction is outputted to the radiation irradiation control device 12 and the reading control device 14, and dynamic imaging is started (Step S4). That is to say, the radiation is irradiated by the radiation source 111 at the pulse interval set in the radiation irradiation control device 12, and the image frames are obtained by the radiation detector 131. When a predetermined time elapses after the start of the dynamic imaging, an instruction to end the imaging is outputted to the radiation irradiation control device 12 and the reading control device 14 by the control unit 21, and the imaging operation is stopped. Note that such a time from the start of the dynamic imaging to the stop of the imaging operation is a time while it is possible to sufficiently image movements of a plurality of breathing cycles.

The image frames obtained by the imaging are sequentially inputted to the imaging console 2, and correction processing is performed for the respective image frames (Step S5). In the correction processing of Step S5, three pieces of correction processing, which are offset correction processing, gain correction processing and defective pixel correction processing, are performed. First, the offset correction processing is performed for the respective obtained image frames, and offset values resulting from dark currents superimposed on the respective obtained image frames are removed. In the offset correction processing, for example, there is performed processing for subtracting a prestored offset correction coefficient from the respective pixel values (gray levels: hereinafter referred to as signal values) of the respective obtained image frames. Here, the offset correction coefficient is an image obtained by averaging a plurality of image frames obtained in advance at the time when the radiation is not irradiated. Subsequently, the gain correction processing is performed, and variations among each pixel, which are caused by individual differences among the respective detection elements corresponding to the respective pixels of the respective image frames and by gain unevenness of a readout amplifier, are removed. In the gain correction processing, for example, processing for multiplying the respective image frames after the offset correction by a prestored gain correction coefficient is performed. Here, the gain correction coefficient is a coefficient, which is calculated in advance from a relationship between an image obtained by averaging the plurality of already-offset-corrected image frames obtained at the time when the radiation is uniformly irradiated onto the radiation detector 131 and an output signal value expected under the radiation irradiation conditions at this time so that the signal values of the respective pixels after the correction can become uniform, followed by storage. Subsequently, the defective pixel correction processing is performed, and pixels in which sensitivity is nonlinear in comparison with peripheral pixels and defective pixels without sensitivity are removed. In the defective pixel correction processing, for example, there is performed processing for, in the respective pixels registered in a prestored defective pixel position information map, replacing signal values of the defective pixels with an average value of signal values of non-defective pixels in the vicinities thereof in accordance with the defective pixel position information map. Here, the defective pixel position information map is a map in which positions of the plurality of defective pixels are registered as a result of the defective pixels recognized from the image frames which are already subjected to the offset correction and the gain correction and are obtained at the time when the radiation is uniformly irradiated onto the radiation detector 131. With regard to the above-described offset correction coefficient, gain correction coefficient and defective pixel position information map, optimal values are individually prestored according to modes of collecting binnings, dynamic ranges and the like, and in such individual collection modes, optimal values corresponding thereto are read out.

Subsequently, the respective image frames after the correction processing and numbers representing imaging orders thereof are stored in association with each other in the storage unit 22 (Step S6), and are displayed on the display unit 24 (Step S7). Here, the image frames and the numbers may be stored after performing logarithmic transformation processing for transforming the signal values of the respective pixels of the respective image frames from antilogarithms to logarithms immediately before storing the respective image frames. The radiographer confirms the positioning and the like by each of the displayed dynamic images, and determines whether an image suitable for the diagnosis is obtained by the imaging (imaging is OK) or it is necessary to perform the imaging one more time (imaging is NG). Then, the radiographer operates the operation unit 23, and inputs a determination result. Note that the respective image frames obtained by the imaging may be collectively inputted after the imaging of all thereof is ended.

When a determination result indicating that the imaging is OK is inputted by a predetermined operation on the operation unit 23 (Step S8; YES), then to each of a series of the image frames obtained by the dynamic imaging, there are added pieces of information such as an identification ID for identifying the dynamic image, patient information, an inspection target area, the radiation irradiation conditions, the image reading conditions, the number representing the imaging order, and an imaging date (for example, these pieces of information are written in a DICOM format into a header region of the image data). Then, the image frames and the pieces of information added thereto are transmitted to the diagnostic console 3 through the communication unit 25 (Step S9). Then, this processing is ended. Meanwhile, when a determination result indicating that the imaging is NG is inputted by a predetermined operation on the operation unit 23 (Step S8; NO), the series of image frames stored in the storage unit 22 is deleted (Step S10), and this processing is ended. Note that such re-imaging will be executed in this case.

[Operation of Diagnostic Console 3]

Next, a description is made of operations in the diagnostic console 3.

Figure 4:
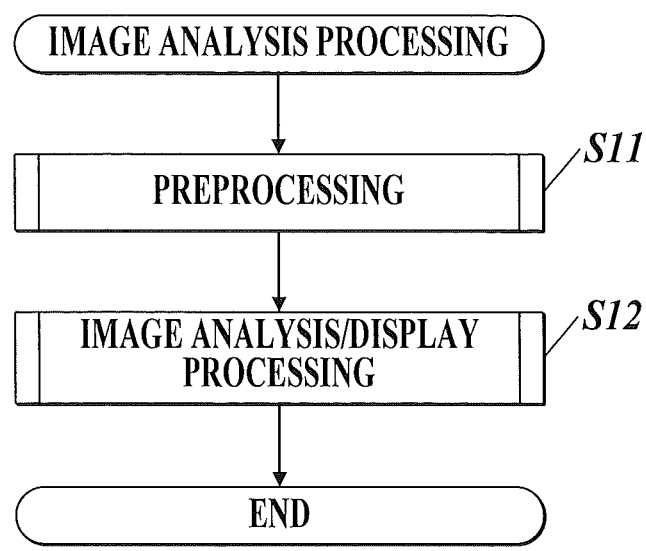
FIG. 4 is a flowchart showing an image analysis processing to be executed by a control unit of a diagnostic console in FIG. 1.

In the diagnostic console 3, when the series of image frames of the dynamic images is received from the imaging console 2 through the communication unit 35, the image analysis processing shown in FIG. 4 is executed by cooperation between the control unit 31 and the image analysis processing program stored in the storage unit 32.

In the image analysis processing, first, preprocessing is performed (Step S11).

Figure 5:
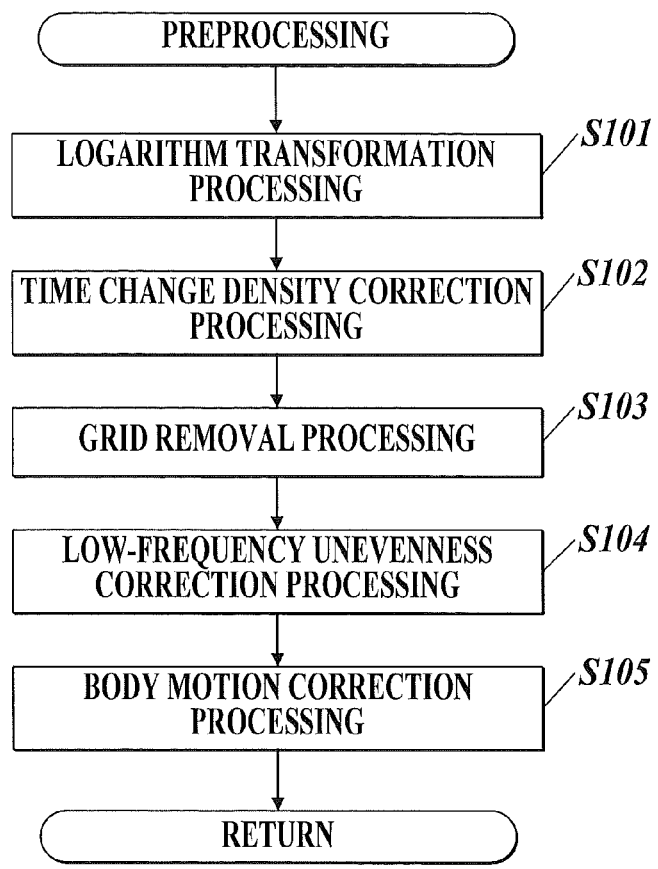
FIG. 5 is a flowchart showing preprocessing to be executed in Step S11 of FIG. 4.

In FIG. 5, a flowchart of the preprocessing to be executed in Step S11 is shown. The preprocessing is executed by cooperation between the control unit 31 and the program stored in the storage unit 32.

In the preprocessing, first, the logarithmic transformation processing is performed, and the signal values of the respective pixels of the respective image frames of the dynamic images are transformed from the antilogarithms to the logarithms (Step S101). Note that in the case where the signals already subjected to the logarithmic transformation are outputted from the radiation detector 131 and the imaging console 2, the step concerned is omitted.

Subsequently, time change signal (density) correction processing (trend correction processing) is performed, and signal values of direct X-ray regions of the respective image frames are corrected so as to become the same value (Step S102).

In Step S102, first, an arbitrary reference image frame is selected from among the series of image frames inputted from the imaging console 2, and a correction value of each image frame is calculated by the following (Expression 1).

Correction value of each image frame=(average signal value of direct X-ray regions of respective image frames)−(average signal value of direct X-ray regions of reference image frame)  (Expression 1)

Subsequently, in each image frame, the correction value calculated by (Expression 1) is subtracted from the signal value for each of the pixels.

Subsequently, grid removal processing is performed for the respective image frames (Step S103). The grid removal processing is processing for removing a striped pattern resulting from a grid array of scattered ray removing grids provided between the subject M (patient) and the radiation detector 131 in order to remove a scattered radiation. The grid removal processing can be performed by using a technology known in public. For example, the grid removal processing can be performed by implementing frequency transformation processing such as the discrete Fourier transform for the respective image frames, thereafter, performing low-pass filter processing therefor to remove high-frequency regions including a frequency of grid images, and implementing the inverse Fourier transform processing therefor (refer to "3. 4 Removal of vertical stripe shadows by grids of X-ray image, Introduction to Medical Image Processing (translated), written by ISHIDA Takayuki). Note that, in the case where the scattered ray removing grids are moving grids (having a mechanism to move the grids in a direction horizontal with respect to a grid surface at the time of the X-ray irradiation), the step concerned may be omitted.

Subsequently, for the respective image frames, low-frequency unevenness correction processing is executed (Step S104). Here, unevenness correction data is prestored in the storage unit 32. The unevenness correction data is data, which is generated based on an imaged image obtained by irradiating the X-ray in the imaging apparatus 1 in a state where the subject is not present, and has a correction value of the signal value of each pixel stored therein. In the low-frequency unevenness correction processing, the unevenness correction data is read out from the storage unit 32, and the correction value of each pixel of each image frame is subtracted from the signal value of the pixel concerned, whereby the unevenness correction is performed.

Subsequently, for the respective image frames, body motion correction processing is performed (Step S105). In the body motion correction processing, the respective image frames are rotated, are moved in parallel, and are positionally aligned with one another so that segments between the X-ray opaque markers M1 and M2 at two spots in all of the image frames can coincide with one another.

When the preprocessing is ended, the processing returns to FIG. 4, and image analysis/display processing is executed (Step S12).

Figure 6:
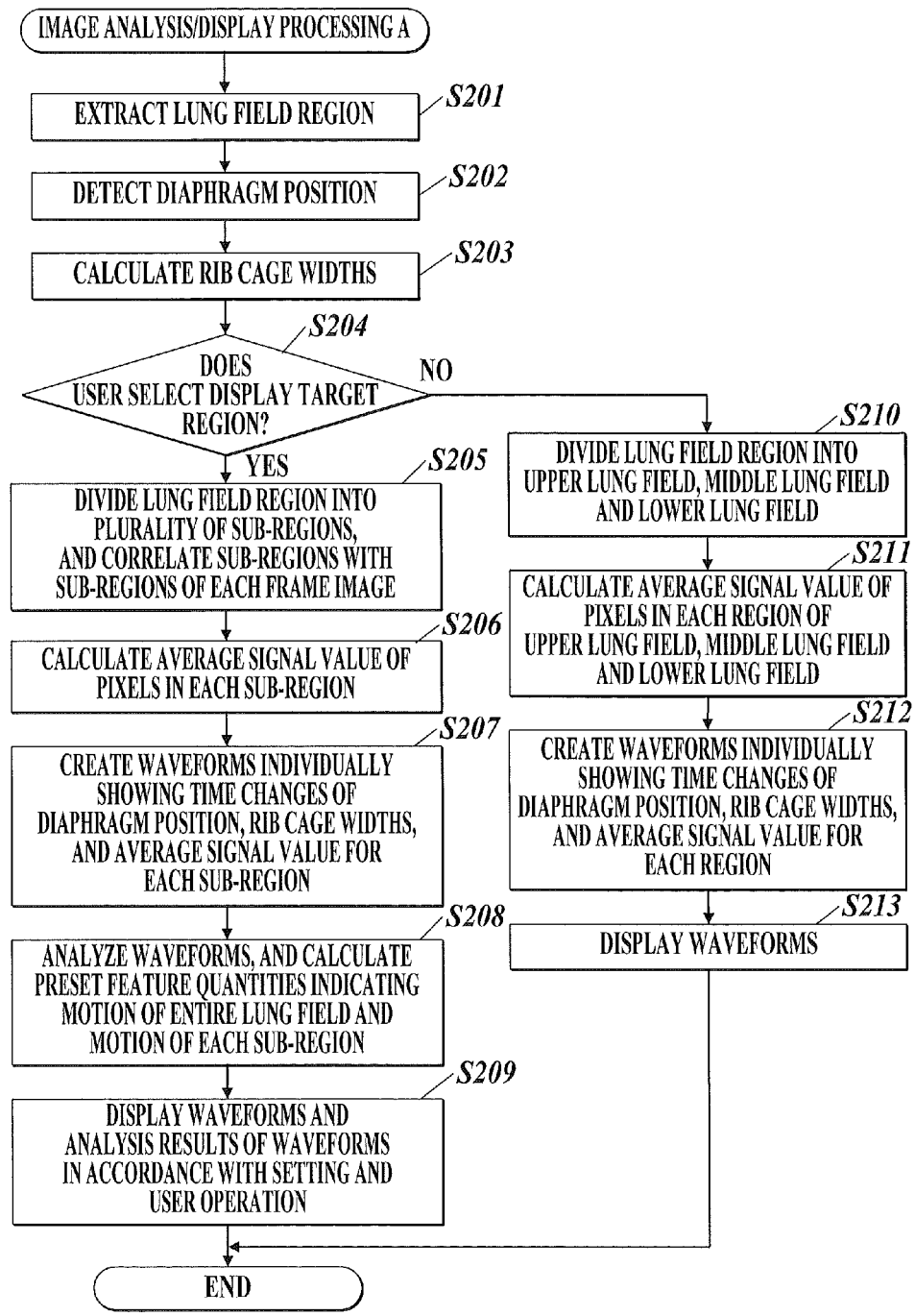
FIG. 6 is a flowchart showing image analysis/display processing A to be executed in Step S12 of FIG. 4.

FIG. 6 is a flowchart showing the image analysis/display processing to be executed in Step S12 of FIG. 4. The image analysis/display processing is executed by cooperation between the control unit 31 and the program stored in the storage unit 32. Note that, for the purpose of a distinction from a second embodiment, the image analysis/display processing in the first embodiment is referred to as image analysis/display processing A.

First, extraction of lung field regions from the respective image frames is performed (Step S201). An extraction method of the lung field regions may be any method. For example, by discriminant analysis, a threshold value is obtained from a histogram of the signal values of the respective pixels in an arbitrary image frame (here, an image frame in which the imaging order is first (earliest)) in a series of image frames, and higher-signal regions than this threshold value in the respective image frames are primarily extracted as lung field region candidates. Subsequently, edge detection is performed in the vicinities of boundaries of the primarily extracted lung field region candidates, and points where edges become maximum in sub-regions in the vicinities of the boundaries are extracted along the boundaries, then in such a way, the boundaries of the lung field regions can be extracted. Information regarding the extracted lung field regions is stored in the RAM of the control unit 31.

Subsequently, detection of diaphragm positions is performed in the respective image frames (Step S202).

Figure 7:
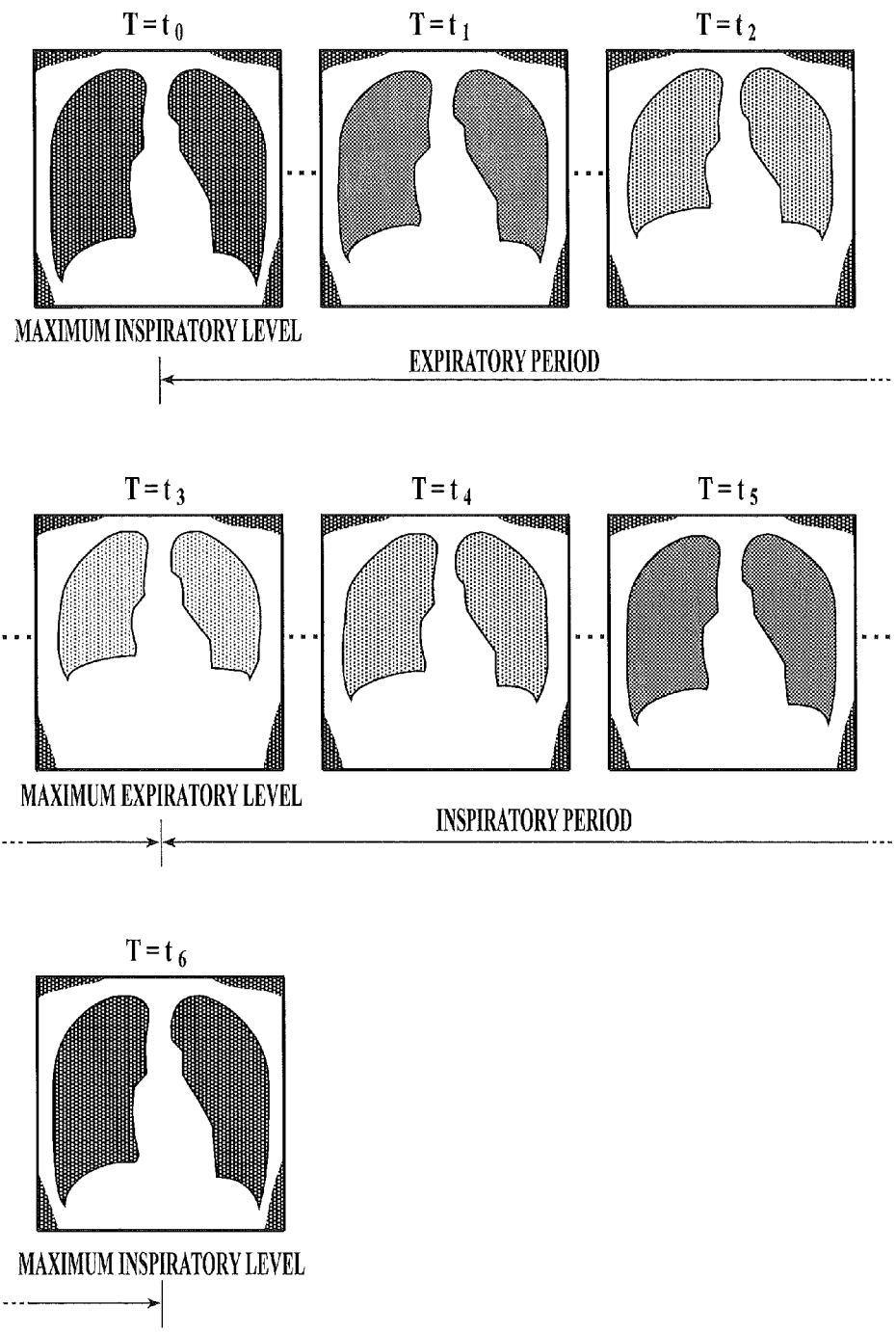
FIG. 7 is a view showing image frames at a plurality of time phases T (T=t0 to t6), which are imaged in one breathing cycle (at a time of deep breathing)

A diaphragm is a muscle that prompts breathing movement of the lungs by vertical movement thereof. In FIG. 7, image frames of a plurality of time phases T (T=t0 to t6), which are imaged in one breathing cycle (at a time of deep breathing), are shown. As shown in FIG. 7, the breathing cycle is composed of an expiratory period and an inspiratory period. In the expiratory period, the diaphragm rises, whereby air is discharged from the lungs, and as shown in FIG. 7, the region (area of the lung field regions) of the lung fields becomes small. At a maximum expiratory level, a state is brought where the diaphragm positions are highest. In the inspiratory period, the diaphragm lowers, whereby the air is taken into the lungs, and as shown in FIG. 7, the region (area of the lung field regions) of the lung fields in a rib cage becomes large. At a maximum inspiratory level, a state is brought where the diaphragm positions are lowest. At the time of the resting breathing, a change of the area of the lung field is smaller than that at the deep breathing shown in FIG. 7; however, motions thereof become similar to those at the deep breathing. At a resting expiratory level (transition point from the expiration to the inspiration at the time of the resting breathing), a state is brought where the diaphragm positions are the highest, and at a resting inspiratory level (transition point from the inspiration to the expiration), a state is brought where the diaphragm positions are the lowest.

Here, as understood also from FIG. 7, vertical positions of lung apexes are hardly affected by the breathing movement, and the positions concerned are hardly changed. Accordingly, it can be said that a distance between each lung apex and the diaphragm in the vertical direction represents a vertical position of the diaphragm. Hence, the distance between the lung apex and the diaphragm in the vertical direction in each image frame of the dynamic image can be obtained as information indicating the diaphragm position.

For example, in Step S202, the following processing is performed for each image frame.

Figure 8:
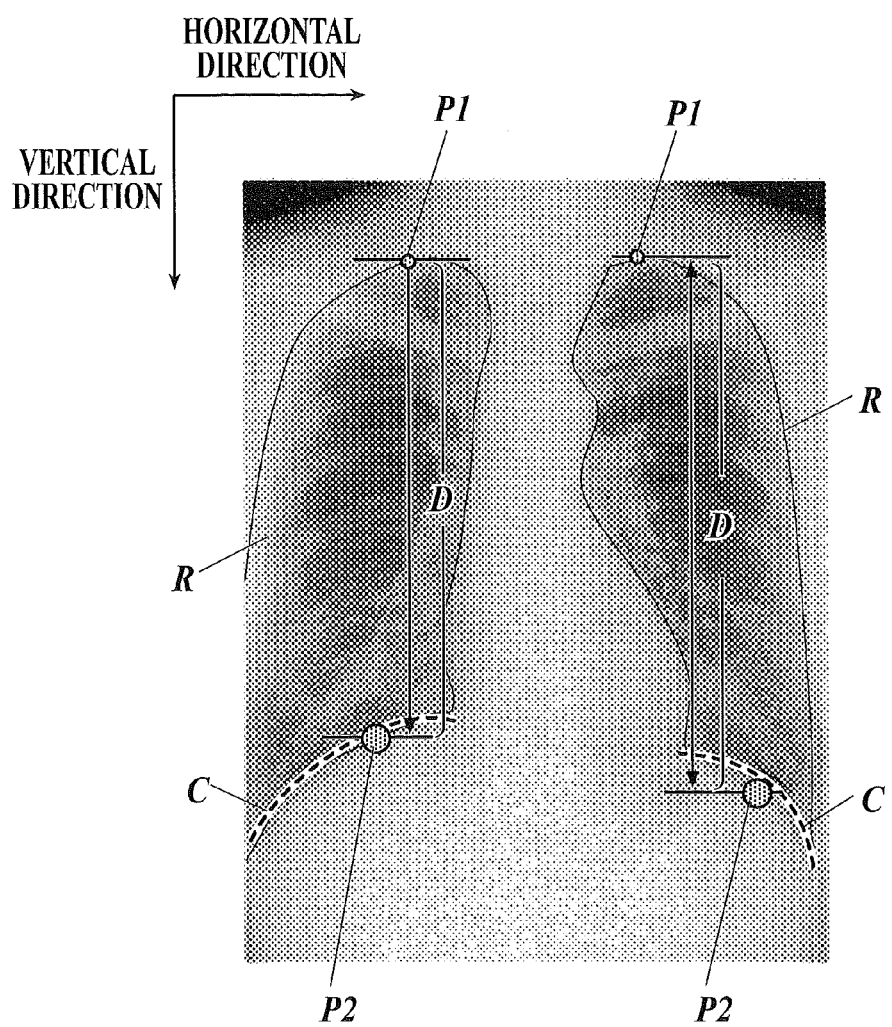
FIG. 8 is a view for explaining calculation of diaphragm positions.

Reference positions P1 and P2 of the lung apexes and the diaphragm are specified from the respective left and right lung field regions (R of FIG. 8). For example, the reference positions P1 of the lung apexes are defined in advance as positions of uppermost ends of the lung field regions R, and positions located uppermost in the vertical direction in the lung field regions R are extracted, whereby the reference positions P1 of the lung apexes are specified. Moreover, the reference positions P2 of the diaphragm are defined in advance as average positions in the vertical direction of curves C (indicated by dotted lines in FIG. 8) of the diaphragm, the curves C of the diaphragm are extracted from the lung field regions R, the average positions thereof in the vertical direction are obtained, and the obtained positions are specified as the reference positions P2 of the diaphragm. Then, distances D between positions (Y coordinates) in the vertical direction, which are the specified reference positions P1 of the lung apexes and the specified reference positions P2 of the diaphragm, are calculated. The calculated distances D are obtained as information indicating the positions of the diaphragm, and are stored in the RAM of the control unit 31.

Subsequently, calculation of widths of the rib cage is performed (Step S203).

Figure 9:
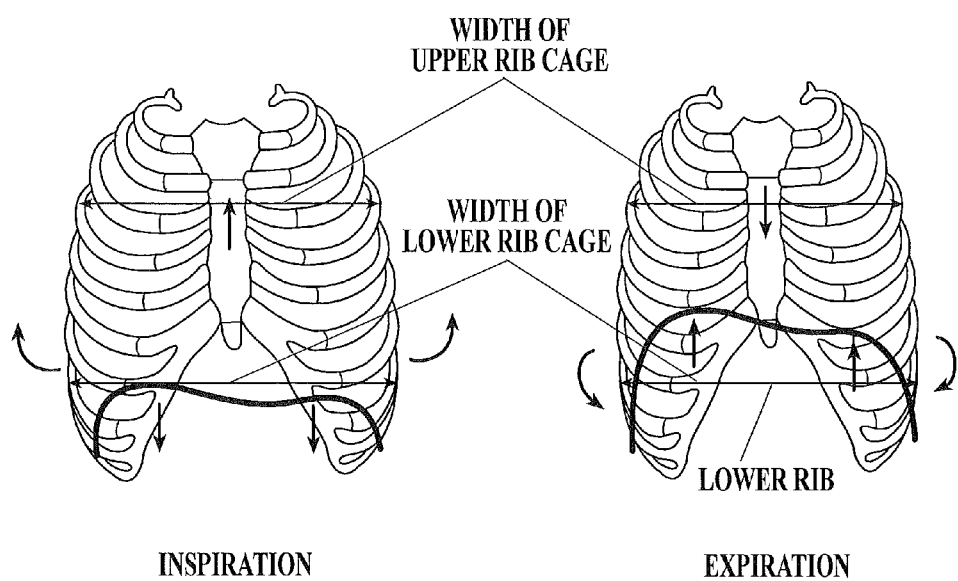
FIG. 9 is a view for explaining calculation of widths of a rib cage.

The rib cage is composed of: an upper rib cage (second to sixth ribs (upper ribs)); and a lower rib cage (seventh to tenth ribs (lower ribs). As shown in FIG. 9, in the inspiratory period, the upper rib cage makes motions to pull the ribs and a sternum upward and to increase an antero-posterior diameter of the rib cage. In the inspiratory period, the lower rib cage makes motions to pull the ribs outer upward and to increase a left-right system of the rib cage. In the expiratory period, the upper and lower rib cages make motions reverse to the above. In Step S203, the respective widths of the upper rib cage and the lower rib cage in each image frame are calculated.

As a calculation method of the widths of the rib cage in Step S203, for example, distances between outside ends (rib cage ends) of the left and right lung field regions at predetermined heights (distance in the vertical direction) from the lung apexes are calculated as the widths (width of the upper rib cage, width of the lower rib cage) of the rib cages in each image frame. As the predetermined heights from the lung apexes, for example, first, for the image frame at the resting inspiratory level or the resting expiratory level, a maximum value of a width (distance between the outside ends of the left and right lung field regions) of the rib cage is calculated, then the respective distances of the upper rib and the lower rib from the lung apexes, which are prestored as functions of this maximum value in the storage unit 32, are read out from the storage unit based on the calculated maximum value, and the widths of the rib cage may be calculated with respect to the readout distances from the lung apexes.

Moreover, the distances of the upper rib and the lower rib from the lung apexes also depend on the patient information such as the sex, the age, the stature and the weight. Accordingly, the patient information (any or a combination of the sex, the age, the stature, and the weight) and the distances of the upper rib and the lower rib from the lung apexes may be prestored as a table in the storage unit in association with each other, the distances of the upper rib and the lower rib from the lung apexes may be read out from the storage unit 32 based on the patient information, and the widths of the rib cage may be calculated with respect to the readout distances from the lung apexes.

Moreover, the ribs may be recognized, and widths of the rib cage at positions of predetermined ribs (for example, a fourth rib as the upper rib, and an eighth rib as the lower rib) may be calculated. As a method for recognizing the predetermined ribs, for example, a method described in the following literature known in public is mentioned. In this method, for the image frame at the resting inspiratory level or the resting expiratory level, first, an edge image is generated by using an edge extraction filter such as a Robinson operator, next, circular arc-like line components which look like the ribs are found by using Hough transform that detects a circular arc shape from an edge image, whereby rib shapes are extracted, and the extracted ribs are counted from the top. In such a way, the predetermined ribs can be recognized ("Edge Extraction for Main Shade of Chest X-Ray Image by Using Hough Transform and Line Shapes (translated)", Journal of The Institute of Electronics, Information and Communication Engineers, D-II, Vol. J77-D-II No. 7 pp. 1375 to 1381).

Information regarding the calculated widths of the rib cage is stored in the RAM of the control unit 31.

Subsequently, the setting information of the display mode, which is stored in the storage unit 32, is read out, and it is determined whether it is set that the user selects the region serving as the display target of the analysis result or it is set that the predetermined region is defined as the display target region (Step S204). When it is determined that it is set that the user selects the display target region (Step S204; YES), the processing shifts to Step S205. When it is determined that it is set that the predetermined region is defined as the display target region (Step S204; NO), the processing shifts to Step S210.

In Step S205, the lung field regions of the respective image frames are divided into the plurality of sub-regions, and the sub-regions of the respective image frames are correlated with one another (Step S205). Positional correspondence relationships of the sub-regions among the respective image frames are stored in the RAM of the control unit 31.

Here, as shown in FIG. 7, the position of each portion of the lung field regions is changed with time by the breathing movement (a positional variation in the vertical direction is larger in a more lower lung field, and moreover, a positional variation of each portion becomes larger as the breathing becomes deeper). That is to say, the positions of the pixels, which indicate the same portion of the lung fields, deviate among the respective image frames. However, in the image imaged at the time of the resting breathing, motions of the lung fields are smaller in comparison with those at the time of the deep breathing shown in FIG. 7, and such a positional deviation with respect to the same portion of the lung fields does not occur to an extent where a large error is generated in the analysis results to be described later.

Figure 11:
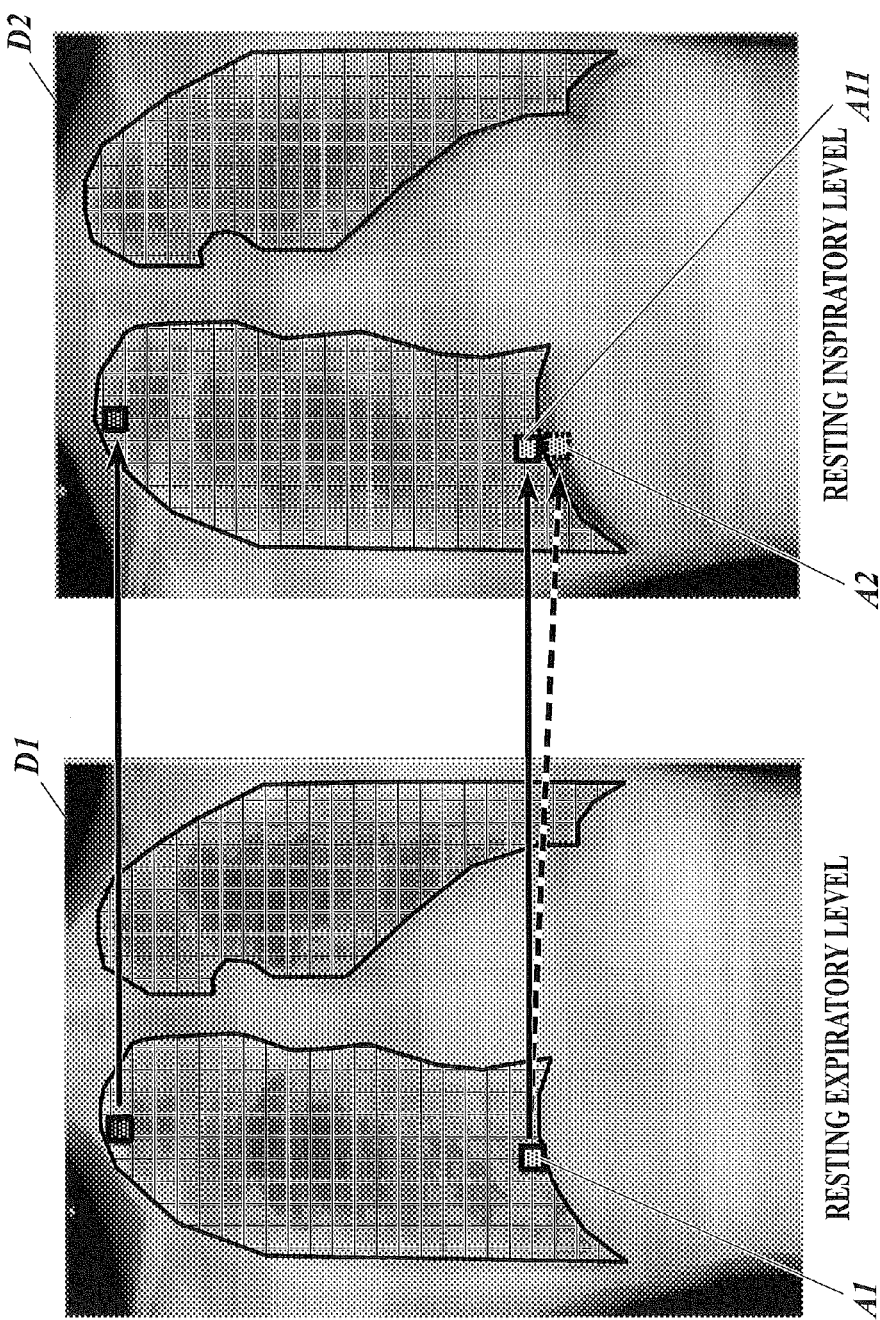
FIG. 11 is a view showing a positional change of a rendered region of the same portion in a lung field between a resting expiratory level and a resting inspiratory level.

An image D1 of FIG. 11 is an image frame at the resting expiratory level (timing when the diaphragm position becomes the highest at the time of the resting breathing). An image D2 of FIG. 11 is an image frame at the resting inspiratory level (timing when the diaphragm position becomes the lowest at the time of the resting breathing). That is to say, the images D1 and D2 of FIG. 11 are images imaged at timing when a shape difference is largest in one breathing cycle. However, in the images D1 and D2 of FIG. 11, it is understood that the positional deviation is slight even in the lower region of such a lung field region in which the positional deviation is the largest (A11 of the image D2 indicates the same pixel position as that of A1 of the image D1, and A2 of the image D2 indicates a region obtained by rendering the same portion as A1 of the image D1 in the lung field).

Figure 10:
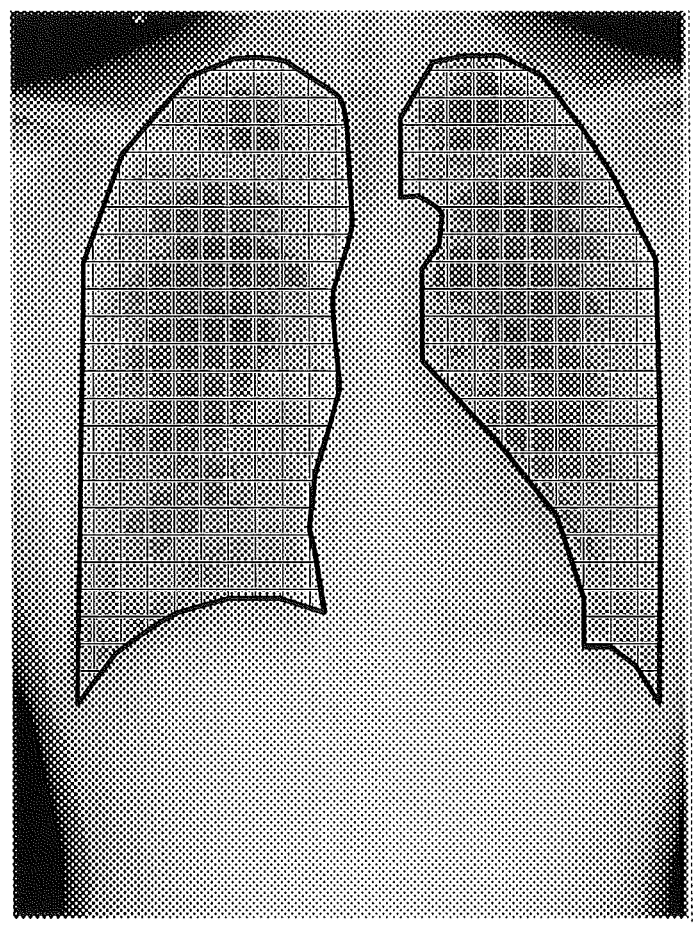
FIG. 10 is a view for explaining division of lung field regions into sub-regions.

Accordingly, as specific processing in Step S205, first, one image frame is set as a reference image from among the series of image frames. Subsequently, extracted lung field regions of the reference image are divided into a plurality of sub-regions (for example, rectangular regions with a square of 0.2 to 4 cm) (refer to FIG. 10). Subsequently, lung field regions of another image frame are divided into sub-regions at the same pixel positions as those of the respective sub-regions of the reference image (that is, the sub-regions are regions with signal values outputted from the same imaging elements of the radiation detector 131). Subsequently, the respective sub-regions at the same pixel positions between the respective image frames are correlated with each other. In this processing, it becomes possible to perform the division and association of the image frames to the sub-regions at a high speed.

As the reference image, it is preferable to use the image frame at the resting expiratory level. At the resting expiratory level, the diaphragm position becomes the highest at the time of the resting breathing. That is to say, the area of each lung field region becomes smallest, and accordingly, when the sub-regions of the reference image are correlated with those of the other image frame, the sub-regions are not correlated with regions outside of the lung field of the other image frame. This is the reason for using the image frame at the resting expiratory level.

Such an image at the resting expiratory level can be obtained by extracting an image, in which the diaphragm position is located at the highest position, from among the series of image frames.

The above-described embodiment is a so-called regarding method, in which one image frame among the series of image frames is set as the reference image, a pixel group of the radiation detector 131, which corresponds to the lung field region extracted by using the reference image concerned, is regarded as a pixel group of the radiation detector 131 which is related to the lung field region also in another image frame, and then subsequent arithmetic operation processing is performed in a unit of pixel of the radiation detector 131.

As opposed to this, as a method for further enhancing analysis accuracy though a processing time is required, such a method is also adoptable, in which accurate association of the actual lung field regions over the series of image frames is achieved by using so-called local matching processing and warping processing.

Figure 12:
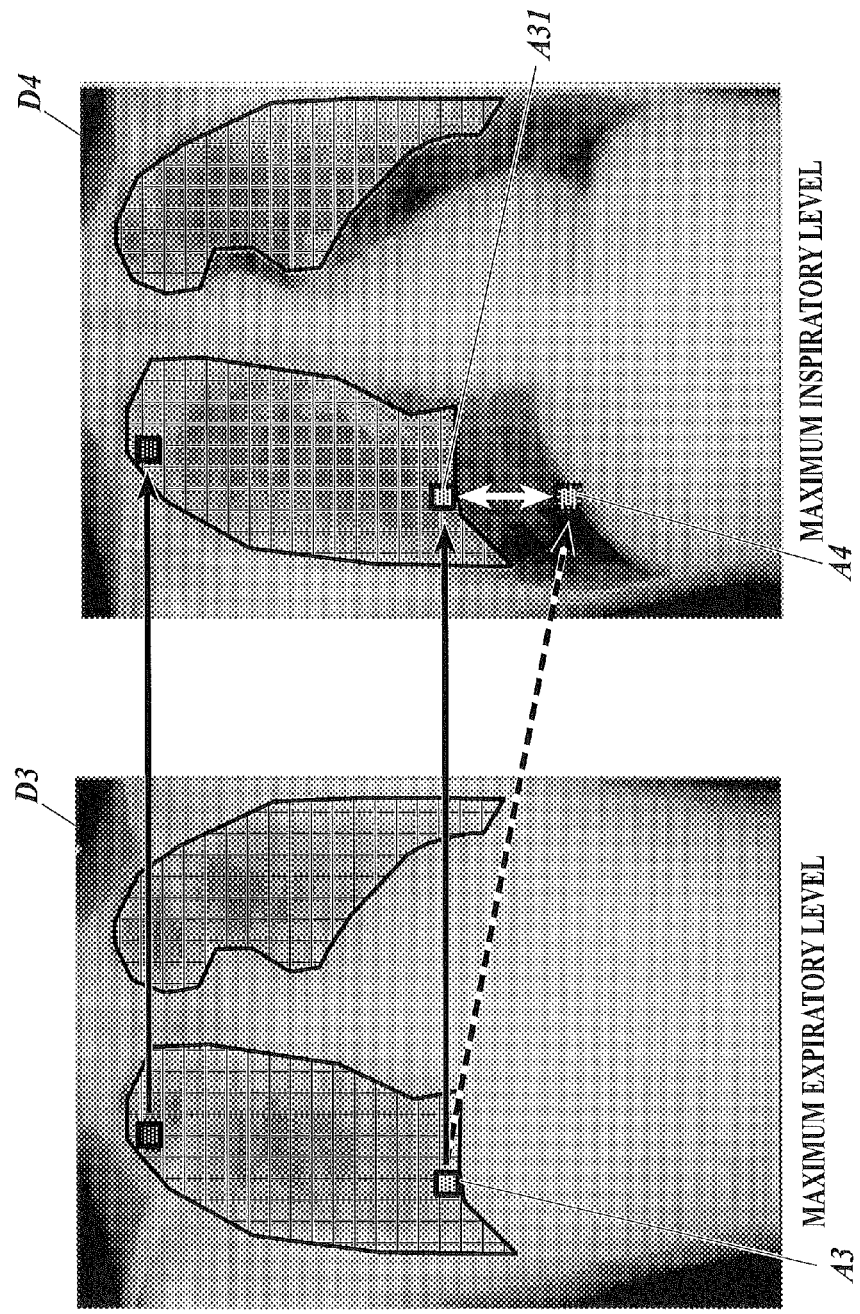
FIG. 12 is a view showing a positional change of the rendered region of the same portion in the lung field between a maximum expiratory level and a maximum inspiratory level.

In the case where the imaged dynamic images are images at the time of the deep breathing, then as shown in FIG. 12, pixel positions which indicate the same portion of the lung field largely deviate from each other. Here, an image D3 of FIG. 12 is an image frame at the maximum expiratory level at the time of the deep breathing, and an image D4 of FIG. 12 is an image frame at the maximum inspiratory level at the time of the deep breathing (A31 of the image D4 indicates the same pixel position as A3 of the image D3, and A4 of image D4 indicates a region obtained by rendering the same portion as A3 of the image D3 in the lung field). Therefore, if the region in each image frame, which is located at the same pixel position as that of each sub-region of the reference image, is defined as the region, which corresponds to the sub-region concerned, in a similar way to the time of the resting breathing, then a large error resulting from a signal value change by the positional deviation occurs in analysis results to be described later, and the analysis results concerned become those unusable for the diagnosis. Accordingly, also in such a case, preferably, corresponding point extraction processing (local matching processing) for extracting corresponding points among the respective image frames and non-linear distortion transformation processing (warping processing) are performed, whereby the regions in which the same portion of the lung field region is rendered are correlated with one another among the respective image frames.

In the local matching processing, first, such a lung field region extracted from the image frame in which the imaging order is first (earliest) is divided, for example, into sub-regions made of rectangles with a square of 0.2 to 4 mm.

Subsequently, the image frame in which the imaging order is first is defined as F1, an image frame adjacent thereto (that is, an image frame in which an imaging order is adjacent (that is, a chronologically adjacent image frame; the same shall apply hereinafter)) is defined as F2, and a seek area of each sub-region of F1 is set in F2. Here, if a coordinate of a center point in each sub-region in F1 is defined as (x, y), then the seek area of F2 is set so as to have the same center point (x, y), and to be larger in longitudinal and lateral widths (for example, by 1.5 times) than the sub-region of F1. Then, for each region of F1, a region where a matching degree becomes highest in a seek range of F2 is obtained, whereby a corresponding position on F2, which corresponds to each sub-region of F1, is calculated. As the matching degree, a least-squares method or cross-correlation coefficient is used as an index thereof. Then, a lung field region of F2 is divided at such corresponding positions of the respective sub-regions of F1.

Subsequently, F2 is regarded as new F1, and an image frame in which an imaging order is next to F2 is regarded as new F2, and corresponding positions of F2 in the respective sub-regions of F1 are calculated. The above-described processing is repeated, whereby to which position of the image frame adjacent to each image frame each sub-region of each image frame corresponds is obtained. Processing results thus obtained are stored in the RAM of the control unit 31.

Subsequently, the warping processing is performed. Specifically, the image frame in which the imaging order is first is defined as F1, the image frame in which the imaging order is adjacent (chronologically adjacent) thereto is defined as F2, and based on the corresponding positions of the respective sub-regions among the adjacent image frames, which are calculated by the above-described local matching processing, a shift vector from F1 to F2 is calculated for each of the sub-regions. Subsequently, the calculated shift vector is subjected to fitting by a polynomial, and a shift vector of each pixel in each sub-region is calculated by using this polynomial. Then, the warping processing is performed based on the calculated shift vector of each pixel, and the position of each pixel in each sub-region of F2 is shifted to a position of the corresponding pixel of the image frame of F1. Subsequently, F2 subjected to the warping processing is newly regarded as F1, and the next image frame in which the imaging order is F2 is regarded as new F2, and the above-described processing is performed. The above-described processing is sequentially repeated between the adjacent frames images in which the imaging orders are earlier, whereby it becomes possible to allow positions of the respective sub-regions of all the image frames to substantially coincide with the image frame in which the imaging order is 1 (that is, the reference image in the local matching and warping processing). Positional correspondence relationships of the sub-regions among the respective image frames are stored in the RAM of the control unit 31.

Subsequently, in each image frame, an average signal value of the pixels in each sub-region is calculated (Step S206). Averaged pixel signal values are stored in the RAM of the control unit 31.

Subsequently, with regard to each of the diaphragm position, the rib cage width and the average signal value of each small region, a waveform showing a time change thereof is created (Step S207). Specifically, a coordinate plane, in which an elapsed time from the start of the imaging is taken on an axis of abscissas, and each value (the value indicating the diaphragm position, the value of the rib cage width, or the average signal value of the pixels) is taken on an axis of ordinates, is created, and points of the elapsed time from the start of the imaging of the each image frame and of the respective calculated values are plotted thereon, whereby the waveform showing the time change of each value is obtained. Moreover, the time change of the average signal value of each sub-region is subjected to filtering by a low-pass filter (for example, with a cutoff frequency of 0.5 Hz) in a time direction, whereby a waveform showing a time change (time change of the ventilation volume) of a signal value indicating the ventilation volume can be obtained. Furthermore, the time change of the average signal value of each sub-region is subjected to filtering by a high-pass filter (for example, with a cutoff frequency of 0.7 Hz) in the time direction, whereby a waveform showing a time change (time change of the blood flow rate) of the signal value indicating the blood flow rate can be obtained. The time changes of the diaphragm position and the rib cage width are feature quantities indicating the motion of the entire lung field. A resultant obtained by performing such low-pass filter processing for the time change of the average signal value of each sub-region is a feature quantity indicating the motion (ventilation) of each sub-region. A resultant obtained by performing such high-pass filter processing for the time change of the average signal value of each sub-region is a feature quantity indicating the motion (blood flow) of each sub-region.

Then, the obtained waveforms are analyzed, and feature quantities (feature quantities of other than the time changes) indicating the motion of the entire lung field and the motion of each sub-region are further calculated (Step S208). With regard to the feature quantity to be calculated for each sub-region, a feature quantity selected in advance by the user through the operation unit 33 is calculated. That is to say, the feature quantity is calculated based on the setting information of the display mode. For example, a feature quantity selected by the user from among the following (1) to (5) is calculated.

Note that one cycle of the breathing refers to a period from timing when the value of the axis of ordinates becomes a minimum value to timing when the value concerned becomes a next minimum value. The inspiratory period (inspiratory time) refers to a period until the value of the axis of ordinates next becomes maximum from minimum. The expiratory period (expiratory time) refers to a period until the value of the axis of ordinates next becomes minimum from maximum. In the case where a plurality of breathing cycles are included in the waveform, a feature quantity for any one thereof may be calculated, or feature quantities in the plurality of cycles may be individually calculated and averaged.

Figure 13:
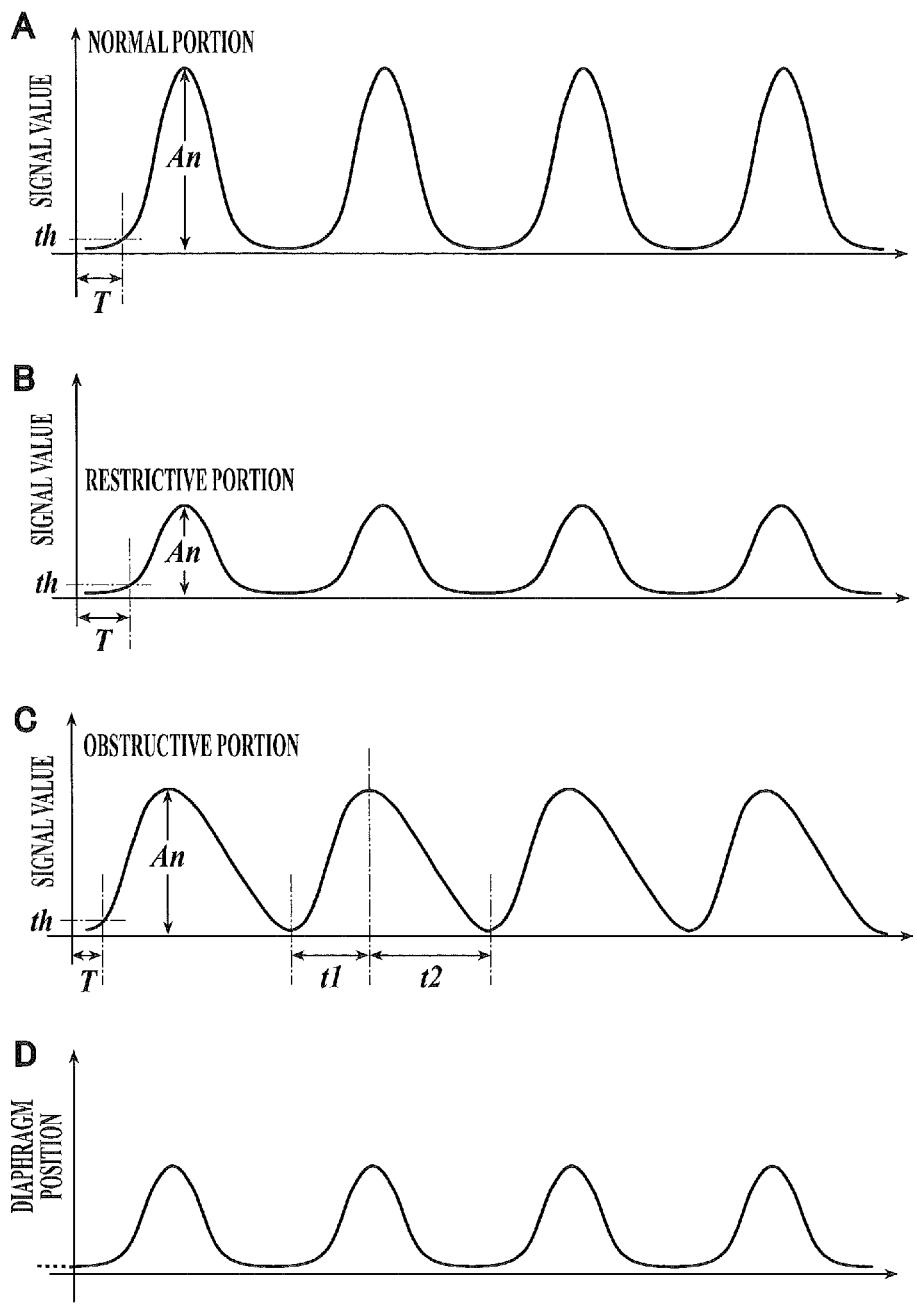
FIG. 13A is a chart showing an example of a waveform representing a time change of a ventilation volume in a sub-region of a normal portion in a certain lung field region.
FIG. 13B is a chart showing an example of a waveform representing a time change of a ventilation volume in a sub-region of a restrictive portion.
FIG. 13C is a chart showing an example of a waveform representing a time change of a ventilation volume in a sub-region of an obstructive portion.
FIG. 13D is a chart showing an example of a waveform representing a time change of the diaphragm position.

Here, FIG. 13 schematically shows the respective waveforms in the case where it is assumed that a normal series and an abnormal series are mixedly present in one patient. FIG. 13A is an example of a waveform showing a time change of a signal value indicating a ventilation volume in a sub-region of a normal portion in a certain lung field region. FIG. 13B is an example of a waveform showing a time change of a signal value indicating a ventilation volume in a sub-region of a restrictive portion. FIG. 13C is an example of a waveform showing a time change of a signal value indicating a ventilation volume in a sub-region of an obstructive portion. FIG. 13D is an example of a waveform showing a time change of the diaphragm position.

(1) Amplitude Of Ventilation Volume

Amplitude (denoted by An in FIG. 13A to FIG. 13C) of the ventilation volume is an index indicating the ventilation volume of each sub-region.

The amplitude of the ventilation volume can be obtained by calculating a difference between a maximum signal value and a minimum signal value in one cycle of the breathing in each waveform showing the time change of the signal value indicating the above-described ventilation volume of each sub-region.

By calculating the amplitude of the ventilation volume of each sub-region, it becomes possible to specify a portion in which a ventilatory function is locally lowered and the ventilation volume is small (the ventilation is not performed sufficiently). For example, with regard to a sub-region in which the amplitude of the ventilation volume is smaller than a predetermined threshold value like sub-regions having the waveforms shown in FIGS. 13B and 13C, it can be determined that a ventilatory function thereof is locally lowered.

Moreover, in the case where variations among such amplitudes of the ventilation volumes of the respective sub-regions are large in the entire lung field, then it is conceived that the portions where the ventilatory function is locally lowered are scattered. In this case, it can be determined that there are suspicions about a local ventilation disorder, for example, such as bulla, emphysema, pneumothorax, atelectasis, pneumonia and pulmonary edema.

Meanwhile, in the entire lung field, in the case where the variations among the amplitudes of the ventilation volumes of the respective sub-regions are small, and the amplitude of the ventilation volume is small as a whole, then it can be conceived that the ventilatory function is lowered uniformly. In this case, it can be determined that there is a suspicion about a restrictive pulmonary disease such as interstitial pneumonitis.

(2) Extended Degree of Expiratory Time with Respect to Inspiratory Time

An extended degree (t1/t2 of FIG. 13C) of the expiratory time with respect to the inspiratory time is an index indicating the motion of each sub-region at the expiratory time.

The extended degree of the expiratory time with respect to the inspiratory time can be calculated by "expiratory time/inspiratory time". The expiratory time can be obtained by calculating a time t2 from the point of time when the signal value becomes the maximum value in one cycle of the breathing to the point of time when the signal value becomes the minimum value therein in the waveform showing the time change of the signal value indicating the above-described ventilation volume. The inspiratory time can be obtained by calculating a time t1 from the point of time when the signal value becomes the minimum value in one cycle of the breathing to the point of time when the signal value becomes the maximum value therein in the waveform showing the time change of the signal value indicating the above-described ventilation volume. Alternatively, the extended degree of the expiratory time with respect to the inspiratory time can also be calculated by "inspiratory maximum differential value/expiratory maximum differential value". The inspiratory and expiratory maximum differential values are obtained by obtaining a difference value of the signal values, which indicate the ventilation volumes for each of the corresponding sub-regions between the adjacent image frames (that is, between the image frames in which the imaging orders are (chronologically) adjacent to each other; the same shall apply hereinafter) in one cycle of the breathing, and by obtaining therein a value in which an absolute value of such an inter-frame difference value becomes maximum in each of the inspiratory period and the expiratory period.

In an obstructive pulmonary disease, in particular, a peripheral airway resistance (viscous resistance) in the expiration is increased, and the expiratory time is increased with respect to the inspiratory time. Therefore, in the entire lung field, a value of the extended degree of the expiratory time with respect to the inspiratory time is increased.

Meanwhile, in the case where variations in the extended degree of the expiratory time with respect to the inspiratory time are large in the entire lung field, it is conceived that there is a suspicion about a mixed pulmonary disease.

(3) Inspiration Start Delay Time

An inspiration start delay time (denoted by T in FIG. 13A to FIG. 13C) is an index indicating lung hardness for each of the sub-regions.

The inspiration start delay time can be obtained in the following manner. First, from the waveform showing the time change of the diaphragm position (distance from the lung apex to the diaphragm), there is obtained timing (time) of the resting expiratory level at which the distance from the lung apex to the diaphragm becomes the minimum value. Subsequently, in the waveform showing the time change of the signal value indicating the ventilation volume of each of the above-described sub-regions, while taking as a reference the minimum value to be obtained at substantially the same timing as the obtained timing, there is obtained timing (time) when a difference between the signal value and the reference concerned becomes a predetermined threshold value th or more. Then, a time between two pieces of the timing obtained as described above is calculated as the inspiration start delay time T. The threshold value th is a signal value uniquely determined based on a noise level with respect to the average signal value in the sub-region, and is a signal value having a magnitude to an extent where a signal change owing to noise is not erroneously recognized as an inspiration start time. This threshold value th may be defined not by the signal value but by a differential value (gradient). At this time, for each sub-region, the inter-frame difference value between the image frames, in which the imaging orders are adjacent to each other, is calculated as the differential value, and a time from the timing when the distance from the lung apex to the diaphragm becomes the minimum value to timing when a differential value of the average signal value of the sub-region taken as the target exceeds this threshold value is calculated as the inspiration delay time.

When the lung is hard, the inspiration delay time T is increased. Accordingly, by obtaining the delay time T of the inspiration start, a portion can be specified, in which the elastic resistance is increased, and the lung is locally hardened. When the inspiration start delay time is large as a whole, it can be determined that there is a suspicion about the restrictive pulmonary disease such as interstitial pneumonitis. When the inspiration start delay time is small as a whole, it can be determined that there is a suspicion about the obstructive pulmonary disease in which the lung is softened.

Note that an expiration delay calculation time may also be calculated.

(4) Inspiratory Flow Rate

An inspiratory flow rate is an index indicating lung softness (lung compliance) for each of the sub-regions.

The inspiratory flow rate can be obtained by calculating a representative value of the differential values at the inspiratory time from the waveform showing the time change of the signal value indicating the above-described ventilation volume of each sub-region. Specifically, in each sub-region, a difference value between the adjacent image frames is obtained, and a representative value of such difference values at the inspiratory time is calculated as the inspiratory flow rate. As the representative value, a maximum value of the differential values at the inspiratory time or an average value of the differential values at the inspiratory time can be defined. Moreover, while focusing a flow rate immediately after the start of the inspiration, a differential value after elapse of a predetermined time from the timing of the resting inspiratory level at which the distance from the lung apex to the diaphragm becomes the minimum value may be defined as the inspiratory flow rate.

When the lung is hard, the flow rate at the inspiratory time is lowered. Accordingly, by obtaining the flow rate at the inspiratory time, the portion can be specified, in which the elastic resistance is increased, and the lung is locally hardened. A portion where the flow rate at the inspiratory time is small is the (restrictive) portion where the lung is hard. A portion where the flow rate at the inspiratory time is large is a (obstructive) portion where the lung is soft. When the inspiratory flow rate is small as a whole, it can be determined that there is a suspicion about the restrictive pulmonary disease. When the inspiratory flow rate is large as a whole, it can be determined that there is a suspicion about the obstructive pulmonary disease.

(5) Amplitude of Blood Flow

The amplitude of the blood flow is an index indicating the blood flow rate of each of the sub-regions.

The amplitude of the blood flow rate can be obtained by calculating a difference between a maximum signal value and a minimum signal value in one cycle of the heartbeat in the waveform showing the time change of the signal value indicating the above-described blood flow rate of each sub-region.

By calculating the amplitude of the blood flow rate of each sub-region, it becomes possible to specify a portion in which a pulmonary blood flow rate is small.

As the feature quantities of the entire lung field, the following (6) to (8) are calculated.

(6) Movement Amount of Rib Position (Upper Rib, Lower Rib)/Diaphragm Position

Movement amount of rib position/diaphragm position are indexes indicating a degree of chest breathing and a restriction degree of the motion of the rib cages.

The movement amount of the upper rib can be obtained by obtaining the maximum value and minimum value of the width of the upper rib in one cycle of the breathing from the waveform showing the time change of the width of the rib cage, and by calculating "maximum value-minimum value" (difference) therebetween. In a similar way, the movement amount of the lower rib can be obtained by obtaining the maximum value and minimum value of the width of the lower rib in one cycle of the breathing from the waveform showing the time change of the width of the rib cage, and by calculating "maximum value-minimum value" (difference) therebetween. The movement amount of the diaphragm can be obtained by obtaining a maximum distance and a minimum distance in one cycle of the breathing from the waveform showing the time change of the above-described distance from the lung apex to the diaphragm, and by calculating "maximum value-minimum value" therebetween.

In the case where "movement of upper rib/movement of diaphragm" is large, that is, in the case where the movement amount of the diaphragm position is small, that is, in the case where the upper chest breathing is dominant, the breathing is performed without using the diaphragm. That is to say, it can be determined that there is a suspicion about a serious chronic ventilator impairment. In the case where the movement amount of the lower rib is small, it can be determined that there is a suspicion about a chronic obstructive pulmonary disease (COPD).

(7) Breathing Rate

A breathing cycle is an index indicating whether or not there is a ventilator impairment.

The breathing cycle can be obtained from the waveform showing the time change of the above-described distance from the lung apex to the diaphragm, and a breathing rate per unit time can be calculated from an inverse number of the breathing cycle. Specifically, a time interval from a minimum value in the waveform showing the time change of the above-described distance from the lung apex to the diaphragm to a next minimum value therein can be calculated as the breathing cycle. Alternatively, the signal values of the entire lung field are averaged, and a waveform showing the time change of the signal value of the entire lung field is obtained, whereby a time interval from a minimum value in the obtained waveform to a next minimum value therein can be calculated as the breathing cycle.

If the breathing movement is normal, then the breathing rate is approximately 15 (12 to 18)/sec. In the case where the breathing rate exceeds this range, it can be determined that there is a ventilator impairment.

(8) Movement Amount of Collarbone

Movement amount of a collarbone is an index indicating a motion of accessory respiratory muscles.

The movement amount of the collarbone can be calculated by recognizing a collarbone region from each image frame, setting a reference point in the recognized collarbone region, and tracking a position of the reference point concerned. In the recognition of the collarbone region, for example, first, for each image frame, an edge image is generated by using an edge extraction filter such as the Robinson operator, then a circular arc-like line that looks like a rib is found by using the Hough transform that detects a circular arc shape from an edge image, whereby a rib shape is detected. Moreover, a straight line portion that looks like the collarbone is found by using Hough transform that detects a straight line, whereby a collarbone shape is detected. The collarbone region is specified based on the collarbone shape thus detected (refer to "Edge Extraction for Main Shade of Chest X-Ray Image by Using Hough Transform and Line Shapes (translated)", Journal of The Institute of Electronics, Information and Communication Engineers, D-II, Vol. J77-D-II No. 7 pp. 1375 to 1381).

In a similar way, movement amount of a shoulder can also be used as the index indicating the motion of the accessory respiratory muscles.

In the case where the movement of the diaphragm is not sufficient, the motion thereof is attempted to be compensated by using the accessory respiratory muscles. In the case of breathing using the accessory respiratory muscles, movement amounts of the collarbone position and the shoulder position are increased. Hence, in the case where the movement amounts of the collarbone position and the shoulder position are large at the time of the resting breathing, it can be determined that the resting breathing is performed by using the accessory respiratory muscles, and it can be determined that there is a suspicion about a serious chronic ventilator impairment.

When the calculation of the feature quantities is ended, the waveforms and the analysis results of the waveforms are displayed on the screen of the display unit 34 based on the set display mode (Step S209).

Figure 14:
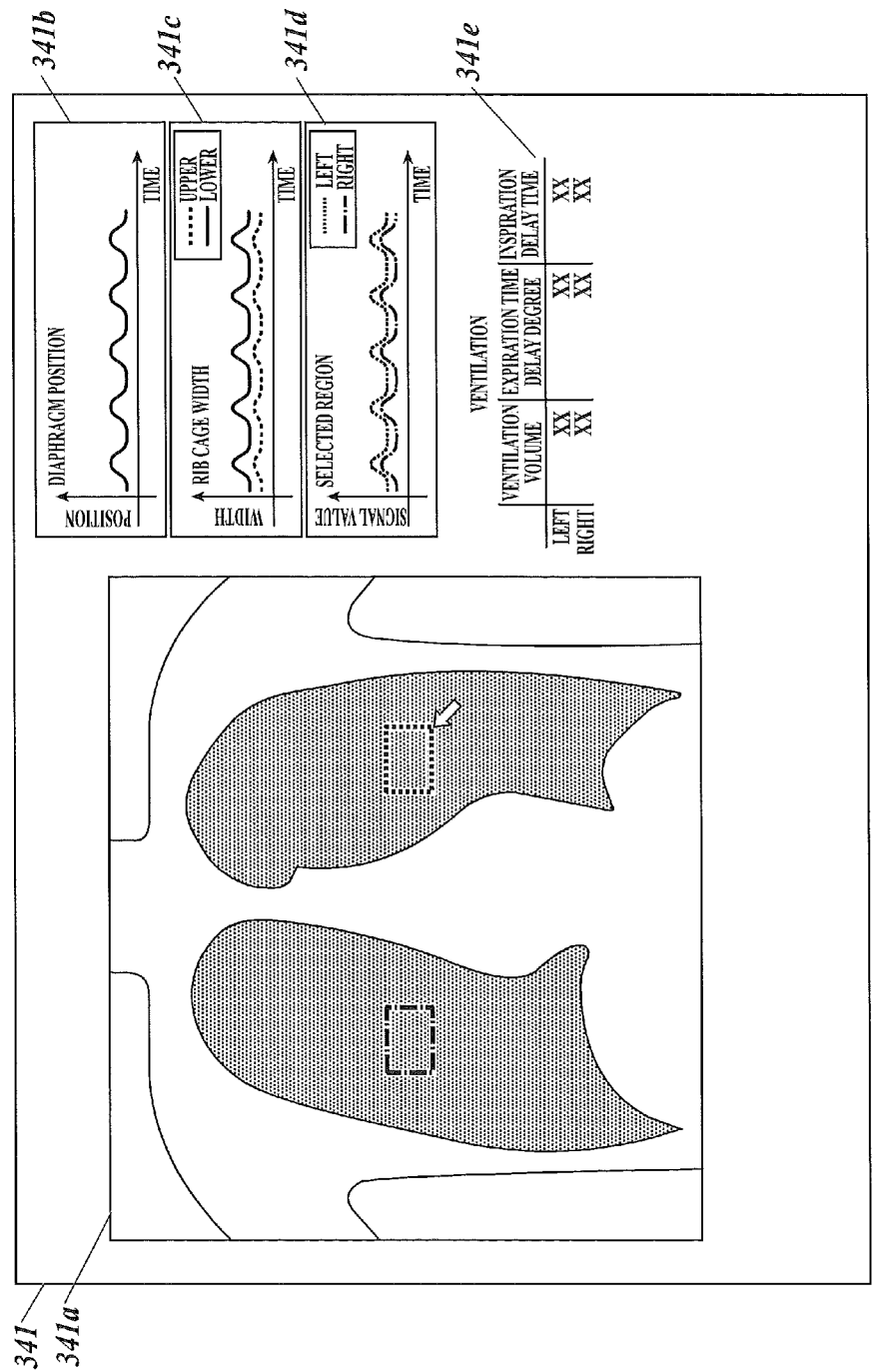
FIG. 14 is a view showing an example of a display screen to be displayed on a display unit in Step S209 of FIG. 6 in a case where display (default) of analysis results of ventilation is set.

In FIG. 14, there is shown an example of a display screen 341 to be displayed on the display unit 34 in Step S209 in the case where display (default) of the analysis results of the ventilation is set. In Step S209, first, there are displayed: one image frame (reference image) 341a among the plurality of imaged image frames; and a waveform 341b showing the time change of the diaphragm position, and waveforms 341c showing the time changes of the rib cage widths, the waveforms 341b and 341c serving as the indexes indicating the motion of the entire lung field. By observing the waveform 341b showing the time change of the diaphragm position and the waveforms 341c showing the time changes of the rib cage widths, for example, the physician as the user can grasp the degree of the chest breathing and the restriction degree of the motion of the rib cages, and can determine whether or not there is a ventilator impairment over the entire lung field.

When one or a plurality of the sub-regions in the lung field region of the reference image 341a is selected by the mouse and the like of the operation unit 33 on the display screen 341, there are displayed: waveforms 341d showing time changes of signal values indicating ventilation volumes in the selected regions; and numeric values 341e of the preset feature quantities therein. Note that xx in FIG. 14 indicates that some numeric values are entered therein (the same shall also apply to FIG. 16, FIG. 17 and FIG. 18). The waveforms 341d and such feature quantity numeric values 341e may be displayed only for a selected region, or as shown in FIG. 14, may be displayed for both of the selected region and a region body axis-symmetric to the region concerned (that is, the left region when the right region is selected, and the right region when the left region is selected). By observing such a waveform 341d regarding the selected region, the physician can grasp whether or not there is a decrease of the local ventilatory function, or the like. Moreover, by confirming the feature quantity numeric values 341e calculated from this waveform 341d, it becomes possible to perform confirmation about the ventilator impairment determined from the waveform. Moreover, it becomes possible to perform the diagnosis by comparing the waveform of the selected region with the waveform of the region horizontally symmetric thereto.

Figure 15A:
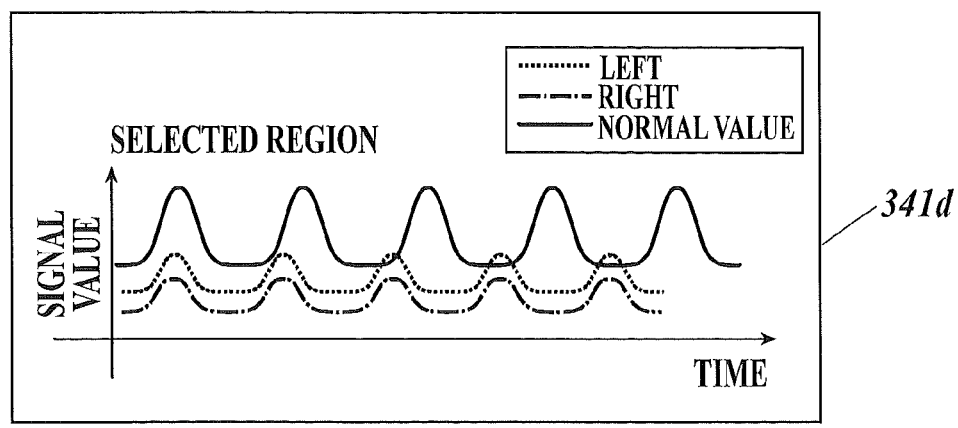
FIG. 15A is a view showing an example where a waveform of a normal case is displayed in parallel to waveforms of selected regions.
Figure 15B:
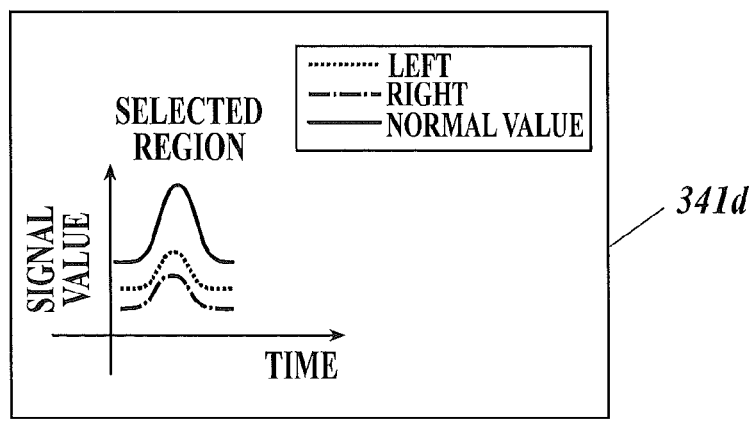
FIG. 15B is a view showing an example where a cycle of the waveform of the normal case is displayed while being allowed to coincide with cycles of waveforms of a patient.

Note that, in order to facilitate the determination of the ventilator impairment in the waveform observation by the physician, a waveform (normal case) showing a normal change of the ventilation volume may be prestored in the storage unit 32, and as shown in FIG. 15A, the waveform of the normal case may be displayed in parallel to such waveforms 341d. Moreover, in order to facilitate the comparison with the waveform of the normal case, as shown in FIG. 15B, the waveform of the normal case may be displayed while being extended and contracted in a time axis direction so that a cycle thereof can coincide with the cycle of the waveform of the patient (the same shall also apply to FIG. 16, FIG. 17, FIG. 18, FIG. 19 and FIG. 21). Moreover, in place of the above-described waveform of the normal case, there may be displayed a waveform of a time change of a signal value for the same region in an image imaged from the same patient in the past.

Figure 16:
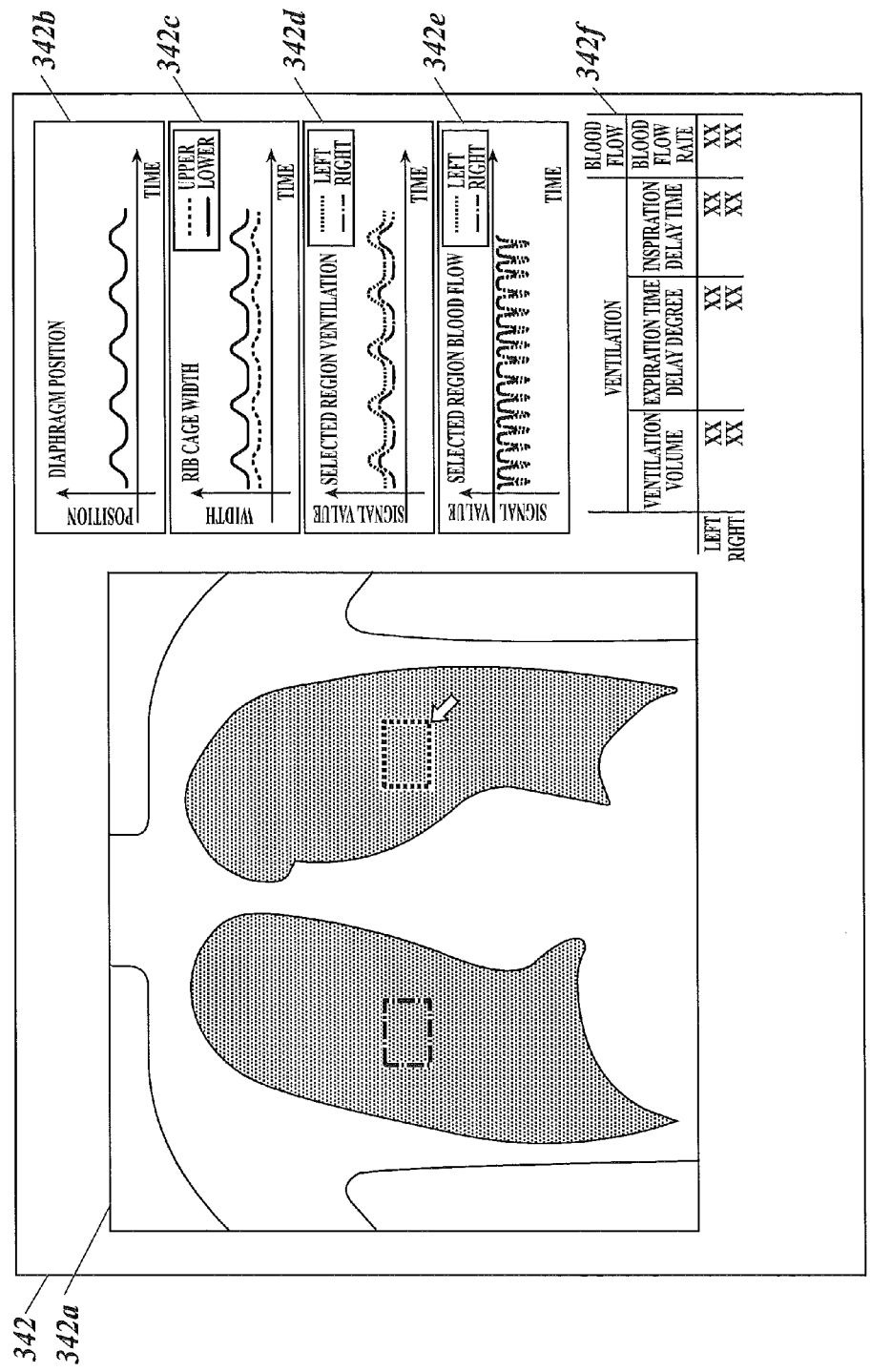
FIG. 16 is a view showing an example of a display screen to be displayed on the display unit in Step S209 of FIG. 6 in a case where display (default) of analysis results of the ventilation and a blood flow is set.

In FIG. 16, there is shown an example of a display screen 342 to be displayed on the display unit 34 in Step S209 in the case where display (default) of the analysis results of the ventilation and the blood flow is set. In Step S209, first, there are displayed: an imaged image frame (reference image) 342a; and a waveform 342b showing the time change of the diaphragm position, and waveforms 342c showing the time changes of the rib cage widths, the waveforms 342b and 342c serving as the indexes indicating the motion of the entire lung field. When one or a plurality of the sub-regions in the lung field region of the reference image 342a is selected by the mouse and the like of the operation unit 33, there are displayed: waveforms 342d showing time changes of signal values indicating ventilation volumes with regard to the selected regions; waveforms 342e showing time changes of signal values indicating blood flow rates with regard thereto; and numeric values 342f of the preset feature quantities. The display screen 342 is a screen, in which the waveforms 342e showing the time changes of the signal values of the blood flow rates and the feature quantities thereof are added to the above-described display screen 341, and accordingly, similar effects to those of the above-described display screen 341 can be exerted. Moreover, pieces of the information about the ventilation and the blood flow are simultaneously displayed, and accordingly, it becomes possible for the physician to grasp the state of the pulmonary disease more accurately. For example, in the COPD, in a portion where the emphysema is deteriorated and a local ventilation disorder portion such as the bulla, a local change (decrease of the blood flow rate) of the blood flow sometimes appears more significantly (that is, corresponds better to the state of the disease). Even in such a case, the diagnosis can be carried out without missing a disorder. Moreover, it also becomes possible to grasp a lesion in which a disorder appears only in the blood flow. For example, it is also possible to carry out such a diagnosis that there is a possibility of pulmonary embolism in the case where the blood flow is small and the ventilation is normal.

Figure 17:
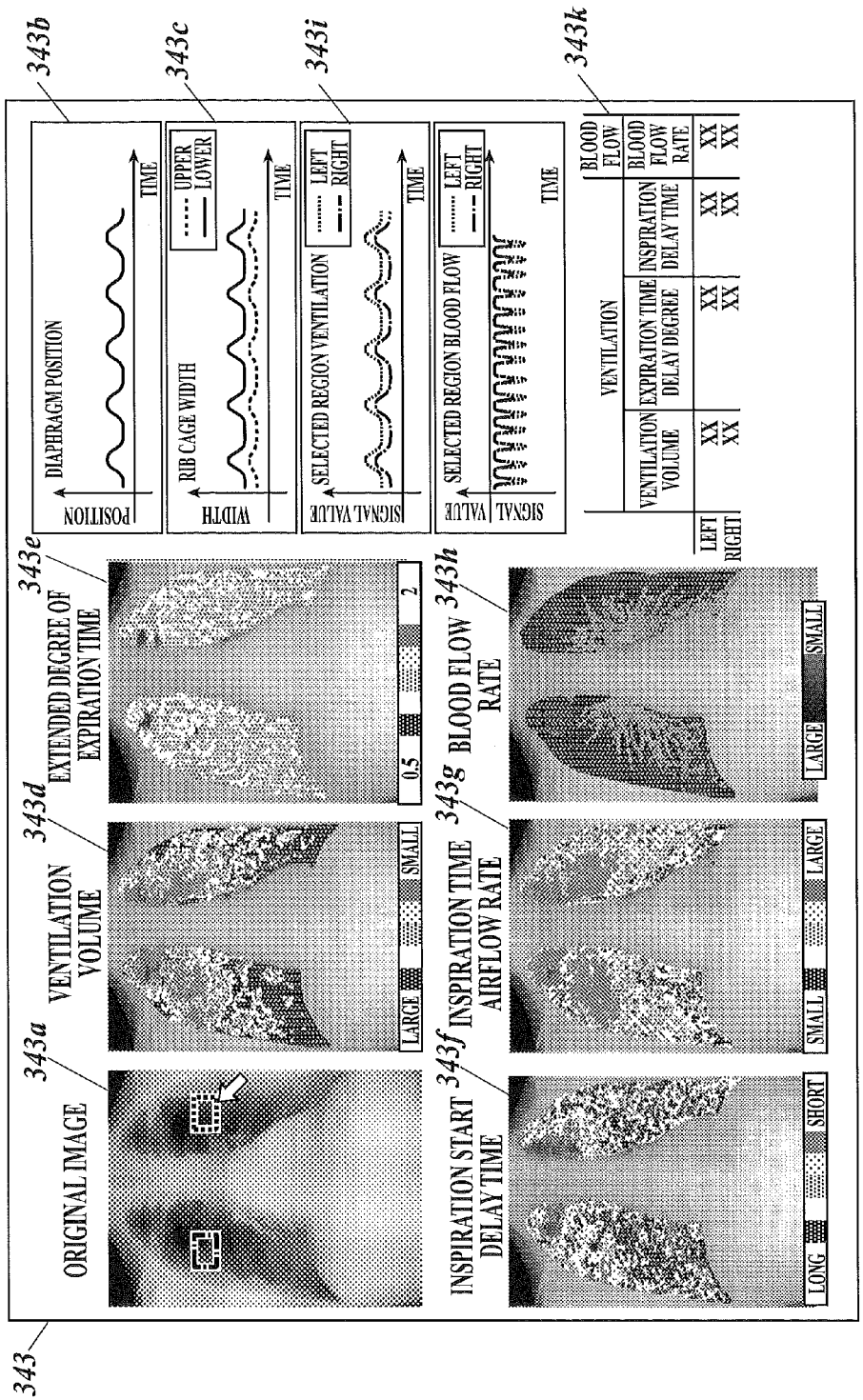
FIG. 17 is a view showing an example of a display screen to be displayed on the display unit in Step S209 of FIG. 6 in a case where list display of analysis results of the respective sub-regions in the lung fields on still images is set as additional information.

In FIG. 17, there is shown an example of a display screen 343 to be displayed on the display unit 34 in Step S209 in the case where list display of the analysis results of the respective sub-regions in the lung fields on still images is set as additional information. In Step S209, first, there are displayed: an imaged image frame (reference image) 343a; a waveform 343b showing the time change of the diaphragm position, waveforms 343c showing the time changes of the rib cage widths, the waveforms 343b and 343c serving as the indexes indicating the motion of the entire lung field; and still images 343d to 343h showing the analysis results of the waveforms of the ventilation volume (ventilation volume and blood flow rate) for each of the sub-regions. In FIG. 17, there is shown an example of display in the case where display of still images of the feature quantities such as the ventilation volume, the extended degree of the expiratory time, the inspiration start delay time, the inspiratory flow rate and the blood flow rate is set as the analysis results of the waveforms. On each of the still images 343d to 343h, a still image formed in the following manner is displayed. First, resultants obtained by calculating values, each of which is of the feature quantity (feature quantity shown in the item) of each sub-region for each cycle of the breathing, over a plurality of cycles, are averaged. Numeric values thus averaged are converted into a display parameter value based on a conversion table of the feature quantity and parameter values at the time of display, which is prestored in the storage unit 32. (Here, for example, the conversion table is a table in which a magnitude of the feature quantity and any one of hue, chroma, brightness, luminance and transparency are correlated with each other in a one-to-one relationship). Then, an image, in which the respective sub-regions are processed by the converted parameter values, for example, are tinted by colors, is overlaid on the above-described reference image. By displaying the still images 343d to 343h, the physician can grasp, by the colors, an overview of the magnitudes of the values of the feature quantity for each of the sub-regions. Then, for example, the physician can specify a sub-region with a local disorder, such as a spot where the ventilation is a little, a spot where the blood flow is a little, and a spot where the delay degree of the expiratory time is large.

When one or a plurality of the sub-regions in the lung field region of the reference image 343a is selected by the mouse and the like of the operation unit 33, there are displayed: waveforms 343i showing time changes of signal values indicating ventilation volumes with regard to the selected sub-regions; waveforms 343j showing time changes of signal values indicating blood flow rates with regard thereto; and numeric values 343k of the feature quantities. The physician observes the above-mentioned still images 343d to 343h. In the case where a sub-region where a disorder is locally present is found, the physician selects the sub-region concerned on the reference image 343a, thus making it possible to confirm a waveform of the sub-region where the disorder is locally present and the numeric values of the feature quantities thereof.

Figure 18:
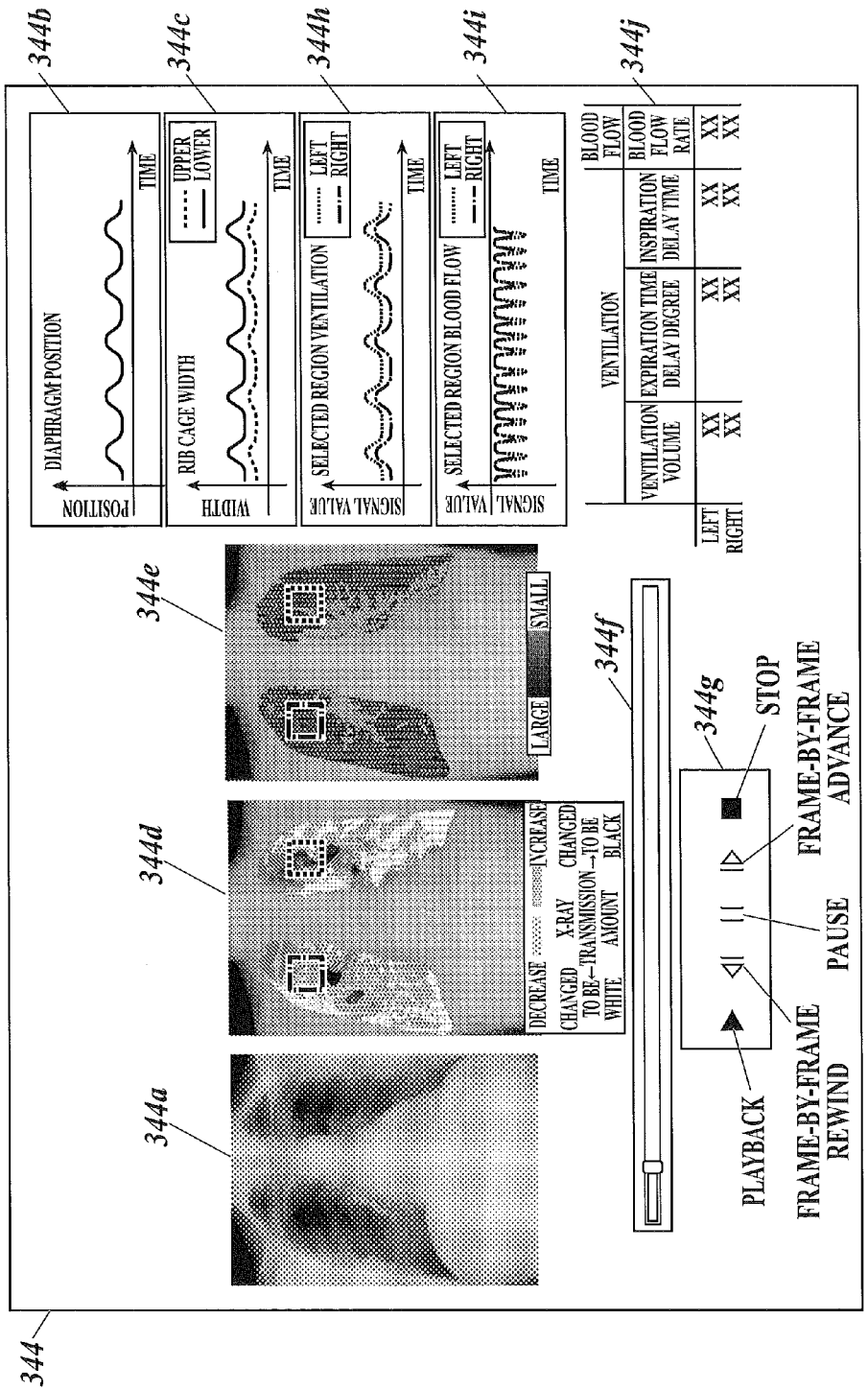
FIG. 18 is a view showing an example of a display screen to be displayed on the display unit in Step S209 of FIG. 6 in a case where moving image display of analysis results of the waveforms is set as additional information.

In FIG. 18, there is shown an example of a display screen 344 to be displayed on the display unit 34 in Step S209 in the case where moving image display of the analysis results of the waveforms is set as additional information. In Step S209, first, there are displayed: an imaged image frame (moving image) 344a; a waveform 344b showing the time change of the diaphragm position, waveforms 344c showing the time changes of the rib cage widths, the waveforms 344b and 344c serving as the indexes indicating the motion of the entire lung field; a moving image 344d showing an analysis result of the waveform of the signal values indicating the ventilation volume; a moving image 344e showing an analysis result of the waveform of the signal values indicating the blood flow rate; an indicator 344f showing an elapsed time of moving image playback; and an operation button 344g for instructing playback, frame-by-frame advance, pause, stop and the like of the moving image. As each of the moving images 344d and 344e, images are formed in the following manner. First, a difference value of the signal value indicating the ventilation volume (blood flow rate) is obtained for each of the corresponding sub-regions between the adjacent image frames. Then, such an obtained inter-frame difference value is converted into a corresponding color based on a conversion table of the magnitude of the feature quantity and the color, which is prestored in the storage unit 32. Then, an image, in which each sub-region is tinted by the converted color, is overlaid on an original image (moving image), and is displayed. By this display, it becomes possible for the physician to observe relationships between the breathing cycle and the ventilation volume and the blood flow rate (that is, changes of the ventilation and the blood flow in the breathing cycle). As a result, it becomes possible for the physician to grasp the state of the disease (as to whether or not there is a disorder; a degree of seriousness) based on physiological behavior.

When one or a plurality of the sub-regions in the lung field region of the moving image 344a is selected by the mouse and the like of the operation unit 33, there are displayed: waveforms 344h showing time changes of signal values indicating ventilation volumes with regard to the selected sub-regions; waveforms 344i showing time changes of signal values indicating blood flow rates with regard thereto; and numeric values 344j of the feature quantities. The physician observes the above-mentioned moving images 344b, 344c and the like. In the case where a region that performs behavior that seems to be a disorder is found, the physician selects such a sub-region concerned on the moving image 344a, thus making it possible to confirm a waveform of the sub-region where such abnormal behavior is locally seen and numeric values of the feature quantities, and to use the waveform and the numeric values as references for diagnosis.

Meanwhile, when it is determined in Step S204 that it is set that the predetermined region is defined as the display target region (Step S204; NO), each of the left and right lung field regions of each image frame are divided into three sub-regions, which are an upper lung field, a middle lung field and a lower lung field (Step S210). For example, the lung field of the reference image is divided into three sub-regions based on the distance in the vertical direction from each lung apex of the reference image to the diaphragm thereof. Subsequently, in each image frame, boundaries are set at the same positions as those of the respective regions in the reference image, and the region division is carried out.

Subsequently, in each image frame, average signal values of the pixels in the respective sub-regions are calculated (Step S211). The average signal values are stored in the RAM of the control unit 31.

Subsequently, individually for the diaphragm position, the rib cage widths and the average signal values of the left and right upper lung fields, middle lung fields and lower lung fields, waveforms showing time changes thereof are created (Step S212). Specifically, a coordinate plane, in which an elapsed time from the start of the imaging is taken on an axis of abscissas, and each value (diaphragm position, rib cage widths, average signal value of the pixels) is taken on an axis of ordinates, is created, and points of the elapsed time from the start of the imaging of the each image frame and of the respective calculated values are plotted thereon, whereby the waveform showing the time change of each value is obtained. Moreover, the time change of the average signal value of each of the upper lung field, the middle lung field and the lower lung field is subjected to the filtering by the low-pass filter (for example, with a cutoff frequency of 0.5 Hz) in the time direction, whereby a waveform showing the time change of the signal value indicating the ventilation volume is obtained.

Subsequently, a display screen that displays such waveforms created as described above is displayed on the display unit 34 (Step S213).

Figure 19:
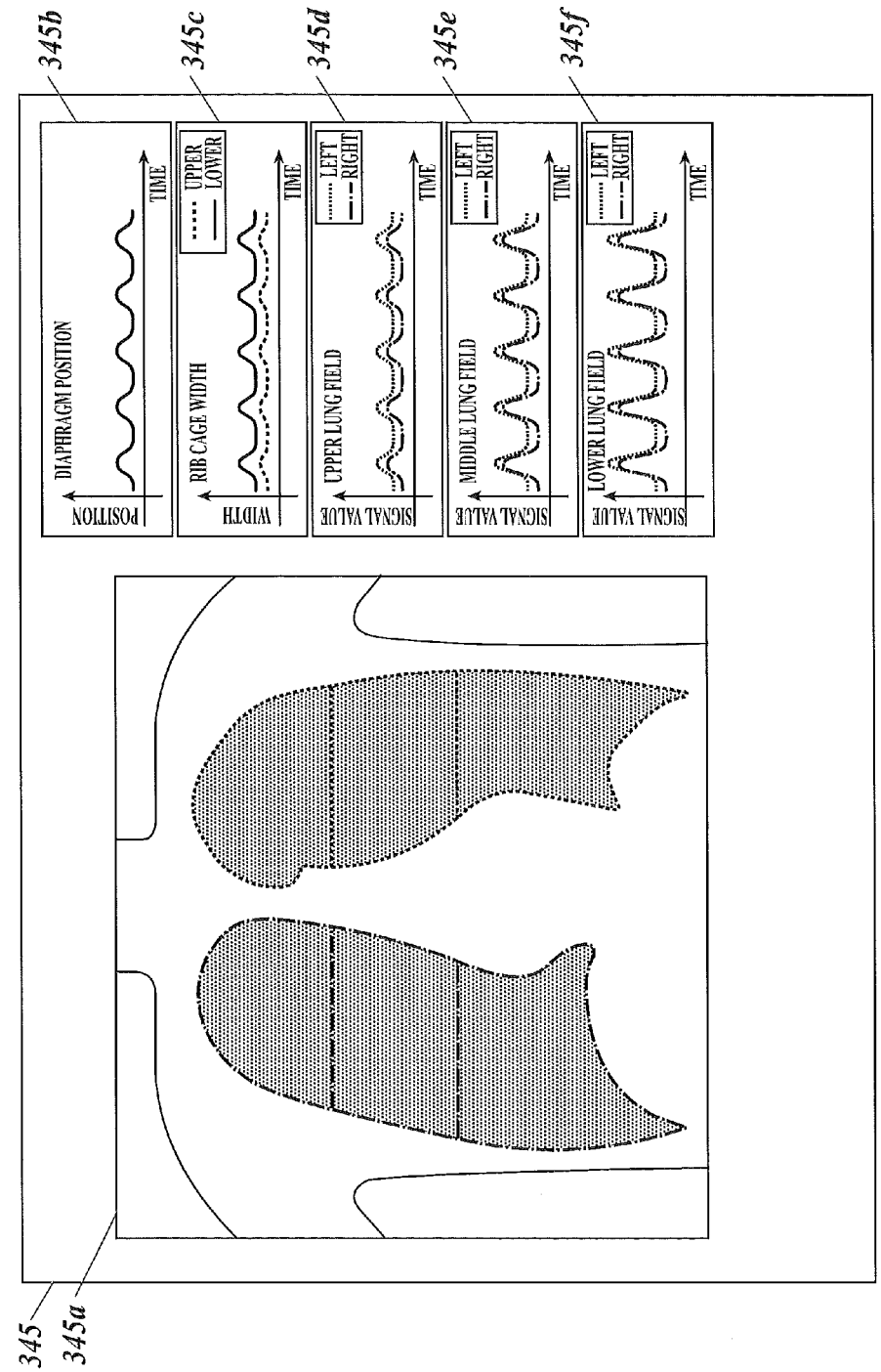
FIG. 19 is a view showing an example of a display screen to be displayed on the display unit in a case where it is selected that a display target region of the analysis results is set (automatically) at a predetermined region.

In FIG. 19, there is shown an example of a display screen 345 to be displayed on the display unit 34 in Step S213. As shown in FIG. 19, on the display screen 345, there are displayed: an image frame (reference image) 345a showing the positions of the respective regions of the upper lung field, the middle lung field and the lower lung field; a waveform 345b showing the time change of the diaphragm position, waveforms 345c showing the time changes of the rib cage widths, the waveforms 345b and 345c serving as the indexes indicating the motion of the entire lung field; and waveforms 345d to 345f showing the time changes of the signal values indicating the respective ventilation volumes of the upper lung field, the middle lung field and the lower lung field. With regard to the waveforms 345d to 345f, the waveforms of the left and right lung fields in each thereof are displayed on the same coordinate space. By observing the waveform 345b showing the time change of the diaphragm position and the waveforms 345c showing the time changes of the rib cage widths, the physician can grasp the degree of the chest breathing and the restriction degree of the motion of the rib cages, and for example, can carry out the diagnosis as to whether or not there is a ventilator impairment over the entire lung field, such as chest breathing dominance and COPD. Moreover, with regard to each of the left and right upper lung fields, middle lung fields and lower lung fields, any of the waveforms 345d to 345f, each of which shows the time change of the signal value indicating the ventilation volume, is observed, whereby it can be grasped whether or not there is a local lowering of the ventilatory function, or the like.

Note that a waveform showing a time change of an average signal value of the whole of one of the lungs may be displayed in combination with the waveform showing the time change of the signal value indicating the ventilation volume for each region of the upper lung field, the middle lung field and the lower lung field. In such a way, the physician can compare a ventilatory function of the whole of the one lung and the ventilatory function of each region with each other, and can observe both thereof. Moreover, the time changes of the signal values indicating the blood flow rates may be calculated, and waveforms obtained therefrom may also be displayed in combination.

The description has been made above of the image analysis/display processing; however, from distributions and average values of the values of the feature quantities in the respective sub-regions, the state of the disease in the entire lung of the subject M may be automatically determined, and a result thereof may be displayed in combination with the above-described display screens 341 to 345.

For example, dispersion of the amplitudes obtained from the sub-regions in the lung field is calculated, and in the case where the dispersion is larger than a predetermined threshold value, it is determined that locally lowered portions of the ventilatory function are scattered. Moreover, an average value of the amplitudes obtained from the sub-regions in the lung field is calculated, and in the case where the calculated average value is smaller than a predetermined threshold value, it is determined that the state of the disease is the restrictive pulmonary disease such as interstitial pneumonitis.

Furthermore, in the case where an average value of the inspiration delay times in the sub-regions in the lung field is larger than a predetermined threshold value, it is determined that the state of the disease is the restrictive pulmonary disease such as interstitial pneumonitis.

In the case where an average value of the inspiratory flow rates in the sub-regions in the lung field is smaller than a predetermined threshold value, it is determined that the state of the disease is the restrictive pulmonary disease such as interstitial pneumonitis.

The above-described predetermined threshold values depend on the sex, the age, the stature and the weight. Accordingly, threshold values corresponding to the sex, the age, the stature and the weight are prestored as a table in the storage unit 32, and based on the patient information (sex, age, stature, weight) inputted in step S1 of FIG. 2, a corresponding threshold value is read out, and is used for the determination of the state of the disease.

<Second Embodiment>

Next, a description is made of a second embodiment of the present invention. In the second embodiment, since contents of the image analysis/display processing to be executed in Step S12 of FIG. 4 are different from those of the first embodiment, a description is made below of image analysis/display processing (image analysis/display processing B) in the second embodiment.

Figure 20:
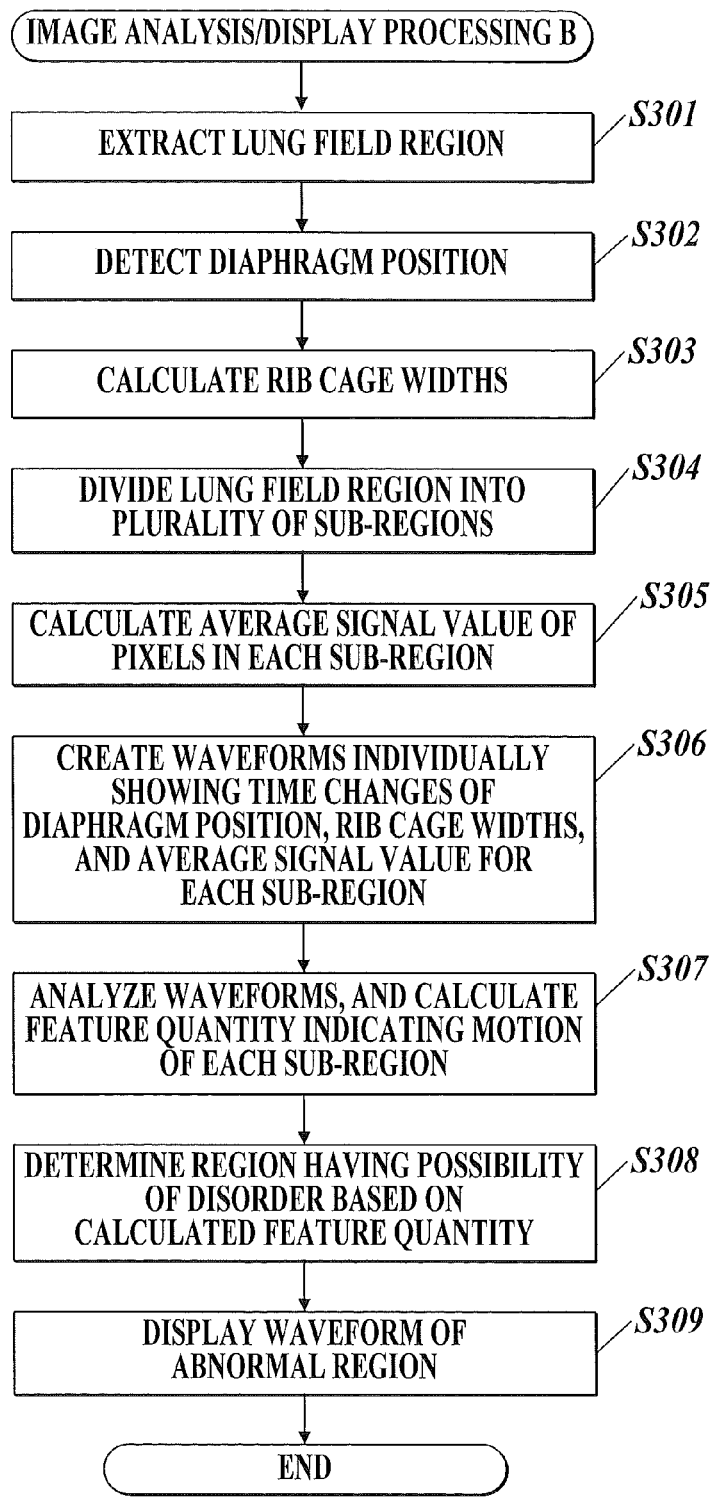
FIG. 20 is a flowchart showing image analysis/display processing B to be executed by the control unit of the diagnostic console of FIG. 1 in a second embodiment.

FIG. 20 is a flowchart of the image analysis/display processing B to be executed by the control unit 31 in Step S12 of FIG. 4. The image analysis/display processing B is executed by cooperation between the control unit 31 and the program stored in the storage unit 32.

First, from the respective image frames, there are performed extraction of the lung field regions (Step S301), detection of the diaphragm positions (Step S302), and calculation of the rib cage widths (Step S303). Pieces of processing of Step S301 to Step S303 are similar to those described in Step S201 to Step S203 in FIG. 6, and accordingly, a description thereof is incorporated by reference herein.

Subsequently, the lung field regions of the respective image frames are divided into a plurality of sub-regions (Step S304). Processing of Step S304 is similar to that described in Step S206, and accordingly, a description thereof is incorporated by reference herein.

Subsequently, in each of the image frames, an average signal value of the pixels in each sub-region is calculated (Step S305).

Subsequently, with regard to each of the diaphragm position, the rib cage width and the average signal value of each small region, a waveform showing a time change thereof is created (Step S306). Specifically, a coordinate plane, in which an elapsed time from the start of the imaging is taken on an axis of abscissas, and each value (the diaphragm position, the rib cage width, the average signal value of the pixels) is taken on an axis of ordinates, is created, and points of the elapsed time from the start of the imaging of the each image frame and of the respective calculated values are plotted thereon, whereby the waveform showing the time change of each value is obtained. Moreover, the time change of the average signal value of each sub-region is subjected to the filtering by the low-pass filter (for example, with a cutoff frequency of 0.5 Hz) in the time direction, whereby a waveform showing the time change of the signal value indicating the ventilation volume can be obtained.

Subsequently, the obtained waveform is analyzed, and a feature quantity indicating the motion of each sub-region is calculated (Step S307). As the feature quantity to be calculated for each sub-region, here, the amplitude of the ventilation volume, the extended degree of the expiratory time, and the inspiratory start delay time, which are described in the first embodiment, are calculated.

Subsequently, based on such feature quantities calculated in Step S307, it is determined whether or not there is a possibility of a disorder in each sub-region (Step S308). For example, in the case where a value of any of the amplitude of the ventilation volume, the extended degree of the expiratory time, and the inspiratory start delay time in each sub-region (1) has a large divergence between the body axis-symmetric regions (horizontally symmetric regions) (that is, has a difference therebetween, which is a predetermined threshold value or more), or (2) exceeds (or falls down below) a predetermined threshold value, it is determined that there is a possibility that the sub-region concerned is abnormal.

Figure 21:
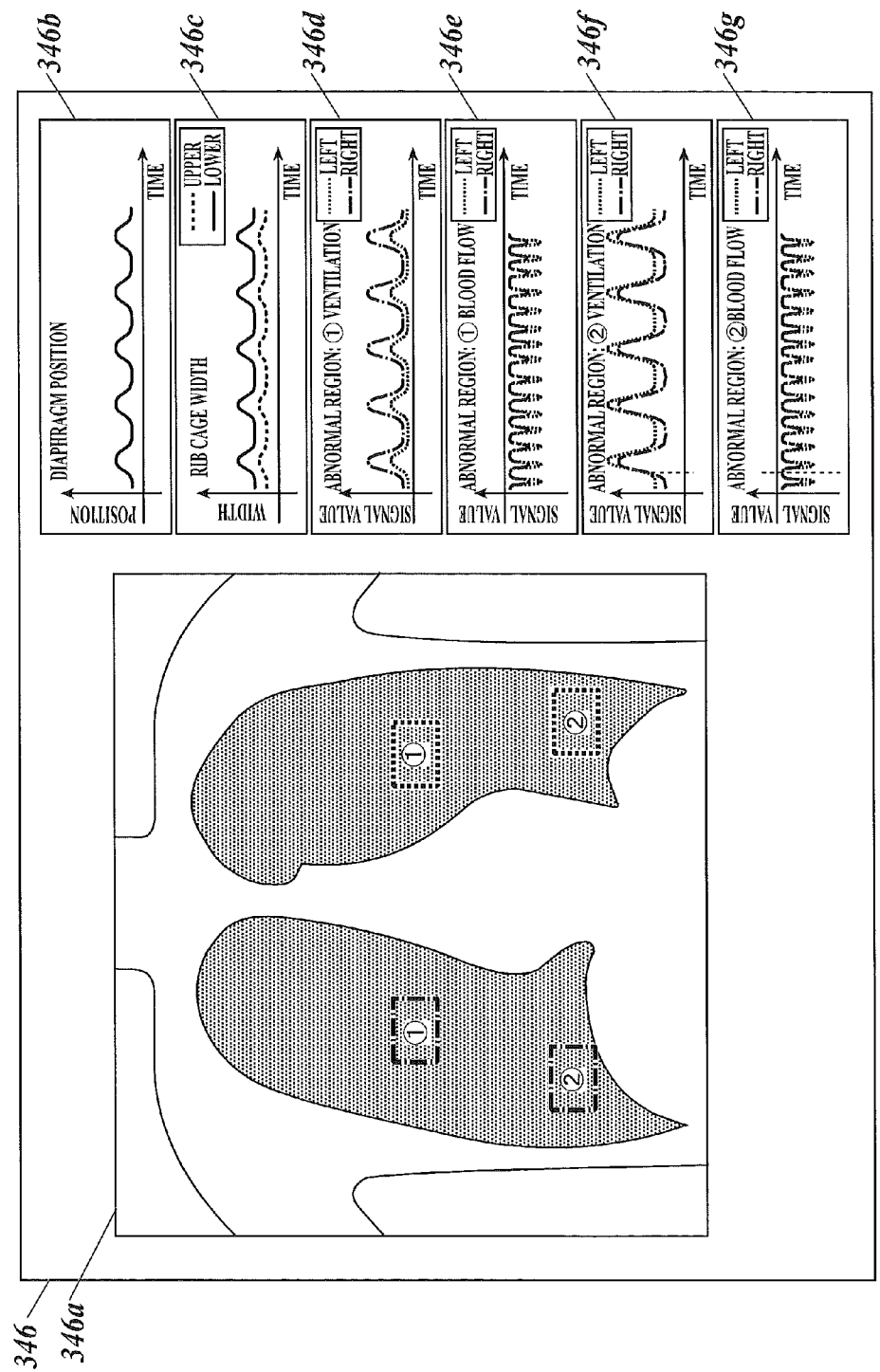
FIG. 21 is a view showing an example of a display screen to be displayed on the display unit in Step S309 of FIG. 20.

Then, on the display unit 34, determination results of the possibility of such a disorder are displayed (Step S309). In FIG. 21, an example of a display screen 346 to be displayed in Step S309 is shown. As shown in FIG. 21, on the display screen 346, there are displayed: a reference image 346a on which annotations are displayed, the annotations surrounding the sub-regions determined to have the possibility of the disorder by colored frames and the like; a waveform 346b showing the time change of the diaphragm position, and waveforms 346c showing the time changes of the rib cage widths, the waveforms 346b and 346c serving as the indexes indicating the motion of the entire lung field; and waveforms 346d and 346f showing waveforms showing time changes of signal values indicating ventilation volumes in the sub-regions determined to be abnormal. Note that, in FIG. 21, as an example, the case where two sub-regions determined to have the possibility of the disorder are detected is taken; however, waveforms corresponding to the number of the respective sub-regions determined to have the possibility of the disorder are displayed. As described above, the regions determined to have the possibility of the disorder are automatically determined, and the waveforms showing the time changes of the signal values indicating the positions of the regions concerned and the ventilation volumes therein are displayed. Accordingly, the physician can efficiently confirm the waveforms of the regions determined to have the possibility of the disorder. At the same time, it becomes possible to reduce the missing of the disease by the physician.

Note that, with regard to the waveforms, not only the waveforms of the time changes of the signal values indicating the ventilation volumes, but also waveforms (waveforms 346e and waveforms 346g of FIG. 21) of the time changes of the signal values indicating the blood flow rate may be displayed in combination. In this case, in Step S306, the time change of the signal value of each sub-region is subjected to the filtering by the low-pass filter (for example, with a cutoff frequency of 0.5 Hz) in the time direction, and in addition, is subjected to the filtering by the high-pass filter (for example, with a cutoff frequency of 0.7 Hz) in the time direction, whereby a waveform showing the time change of the signal value indicating the blood flow rate is obtained. In Step S307, the amplitude of the ventilation volume, the extended degree of the expiratory time, the inspiration start delay time and the amplitude of the blood flow are calculated. In Step S308, in the case where the value of any of the amplitude of the ventilation volume, the extended degree of the expiratory time, the expiration start delay time and the amplitude of the blood flow in each sub-region (1) has a large divergence between the body axis-symmetric regions (horizontally symmetric regions) (that is, has a difference therebetween, which is the predetermined threshold value or more), or (2) exceeds (or falls down below) the predetermined threshold value, it is determined that there is a possibility that the sub-region concerned is abnormal. Then, in Step S309, as shown in FIG. 21, the waveforms of the signal values indicating the blood flow rates are displayed in combination with the waveforms showing the ventilation volumes of the regions determined to have the possibility of the disorder.

As described above, the pieces of information about the ventilation volume and the blood flow are simultaneously displayed, whereby it becomes possible for the physician to grasp the state of the pulmonary disease more accurately. For example, in the COPD, in the portion where the emphysema is deteriorated and the local ventilation disorder portion such as the bulla, the local change (decrease of the blood flow rate) of the blood flow sometimes appears more significantly (that is, corresponds better to the state of the disease). Even in such a case, the diagnosis can be carried out without missing a disorder. Moreover, it also becomes possible to grasp the lesion in which a disorder appears only in the blood flow. For example, it is also possible to carry out such a diagnosis that there is a possibility of the pulmonary embolism in the case where the blood flow is small and the ventilation is normal.

Moreover, the respective feature quantities thus calculated may be integrally determined, a state of disease (case name) of the region determined to have the possibility of the disorder (abnormal region) may be estimated, and the estimated state of disease may be displayed in combination on the display screen 346 and the like. Moreover, a correspondence relationship between the state of disease and the color may be prestored in the storage unit 32, and the abnormal region on the reference image 346a may be displayed by the color corresponding to the estimated state of disease. In such a way, it becomes possible to provide the physician with more detailed diagnosis assisting information about the state of disease. With regard to the estimation of the state of disease, for example, the state of disease can be estimated based on combinations of classifications of the respective feature quantities in such a manner that the respective feature quantities, which are calculated in Step S307 described above, are classified into large, medium and small based on whether or not the feature quantities exceed the predetermined threshold values. In the following (Example 1) and (Example 2), examples of estimation criteria of the state of disease are shown.

EXAMPLE 1

Ventilation volume (amplitude): small, extended degree of expiratory time: small, inspiration start delay time: large (inspiratory flow rate: small), blood flow rate: small→restrictive portion

EXAMPLE 2

Ventilation volume (amplitude): small, extended degree of expiratory time: large, inspiration start delay time: small (inspiratory flow rate: large), blood flow rate: small→obstructive portion As the threshold values of the respective feature quantities in the event of performing the disorder determination for each sub-region, for example, values calculated based on normal values (standard values) are used.

In each sub-region, in the case where the amplitude (ventilation volume), the delay time, the (inspiratory) flow rate and the blood flow rate are normal, these items have trends from the lung base toward the upper lung field, and as going toward the upper lung field, the amplitude becomes smaller, the delay time becomes larger, the (inspiratory) flow rate becomes smaller, and the blood flow rate becomes smaller.

Accordingly, with regard to the above-described respective feature quantities, normal values (standard values) thereof are prestored. Here, the normal values correspond to a vertical position tr from the lung base. (The vertical position tr is defined as a percentage [%] of the vertical position of the local region as a target, which takes the lung base as a reference, with respect to a length of the lung field at the resting inspiratory level.) Moreover, the normal values here are defined to be normal values with respect to average values obtained by averaging, in the horizontal direction, feature quantities of a plurality of the sub-regions in which vertical positions from the lung base are substantially the same. Furthermore, since the respective feature quantities depend on the sex, the age, the stature and the weight, the normal values of the respective feature quantities for the vertical position from the lung base are prestored as a table in the storage unit 32 in response to the sex, the age, the stature and the weight. Then, based on the patient information (sex, age, stature, weight) inputted in Step S1 of FIG. 2, and on the vertical position of the target sub-region from lung base, normal values corresponding thereto are read out, and for example, values of the corresponding normal values±20% (−20% in the case of making comparison with lower limits, +20% in the case of making comparison with upper limits) are used as threshold values of the disorder determination.

As the normal values corresponding to the sex, the age, the stature and the weight, for example, average values of the respective feature quantities with respect to the vertical position from the lung base can be calculated from data of a plurality of able-bodied persons for the respective groups different in sex, age, stature and weight. The average values thus calculated can be used as the normal values.

As described above, in accordance with the diagnosis assistance system 100 according to the present invention, the control unit 31 of the diagnostic console 3 extracts the lung field regions from the respective image frames of the plurality of image frames, which are transmitted from the imaging console 2 and show the movements of the chest portion, divide the extracted lung field regions into the plurality of sub-regions, and analyze the divided sub-regions in association with one another among the plurality of image frames, and thereby calculate the preset feature quantities indicating the motions of the divided sub-regions. Then, when the region that serves as the display target of the analysis result is selected by the operation unit 33, the feature quantities regarding the selected sub-region are displayed.

Hence, the user as the physician selects the sub-regions in the lung field by the operation unit 33 as if using the stethoscope, and can thereby obtain the feature quantities indicating the motions of the selected sub-regions. As described above, in accordance with the diagnosis assistance system 100, there can be provided the GUI-containing system that integrates the information for use in the diagnosis into the visual series, and enables even the physician, who has little experience with the stethoscope, to carry out the accurate diagnosis.

Moreover, the control unit 31 further calculates the predetermined feature quantities regarding the entire lung field, and on the display unit 34, simultaneously displays the feature quantities indicating the motion of such a region selected by the operation unit 33 and the feature quantities indicating the motion of the entire lung field, and accordingly, it becomes possible to grasp the information related to the diagnosis, which is regarding both of the entire lung field and the selected local region, at one time.

Furthermore, the control unit 31 calculates one or a plurality of the feature quantities indicating movement of each sub-region, and accordingly, it becomes possible for the physician to obtain the one or plurality of feature quantities regarding the selected sub-region.

Moreover, such a configuration is adopted, which is capable of selecting one or a plurality of the sub-regions, which serve as the display targets of the analysis results, by the operation unit 33 from the image frames of the still images displayed on the display unit 34. In such a way, it becomes possible for the user to select the one or plurality of regions by an operation as easy as an operation of using the stethoscope, and to display the analysis results of the region concerned.

Moreover, such a configuration is adopted, which is capable of selecting one or a plurality of regions, which serve as the display targets of the analysis results, by the operation unit 33 from the moving image displayed on the display unit 34. In such a way, it becomes possible for the user to easily select one of a plurality of sub-regions, which perform the behavior that seems to be the disorder, by viewing the moving image, and to allow display of the analysis results of the region concerned.

Moreover, on the display unit 34, one of the plurality of image frames is further displayed as a still image, and each sub-region of the image frame concerned is displayed by the color corresponding to the value of the calculated feature quantities, whereby it becomes possible for the user to grasp the feature quantities in each sub-region at a glance, and to thereby easily grasp the local disorder spot in the entire lung field.

Moreover, as the feature quantities indicating the motion of the sub-region selected by the operation unit 33, the time change of the ventilation volume (and the blood flow rate) is displayed as the waveform, whereby it becomes possible for the user to easily grasp the time changes of the ventilation and the blood flow regarding the selected region.

Moreover, in the case where one of the lung field regions is selected by the operation unit 33, the feature quantities of the other lung field region, which is body axis-symmetric to the selected region, are displayed simultaneously with the feature quantities of the selected region. In such a way, the comparison of the feature quantities between the left and right target regions can be easily performed, and information useful for the diagnosis can be provided to the user.

Moreover, such a configuration is adopted, which is capable of selecting the feature quantities, which are to be calculated, from among the plurality thereof in advance by the operation unit 33. In such way, it becomes possible for the user to allow display of a desired feature quantity.

Note that the description in the above-mentioned embodiments is merely an example of a preferred diagnosis assistance system according to the present invention, and the present invention is not limited to this.

For example, in the above-described embodiments, as the waveform showing the ventilation volume for each of the sub-regions, the graph is displayed, in which the signal value indicating the ventilation volume is taken on the axis of ordinates, the time is taken on the axis of abscissas, and the points are plotted; however, a display method of the waveform is not limited to this. For example, a graph may be displayed, in which a differential value (signal value/S) of the signal value, which is equivalent to an airflow rate, is taken on an axis of ordinates, the signal value indicating the ventilation volume is taken on the axis of abscissas and points are plotted. This is a graph equivalent to a spirometric flow volume curve, and accordingly, it becomes possible for the physician to read the diagnostic information in much the same way as in spirometry.

Moreover, in the above-described embodiments, the respective sub-regions are analyzed in advance to calculate the feature quantities, and the analysis results (waveform, values of feature quantities) regarding the sub-region selected by the operation unit 33 are displayed; however, the region selected by the operation unit 33 may be analyzed to calculate the feature quantities.

Moreover, in the above-described embodiments, the waveform showing the time change of the diaphragm position and the waveforms showing the time changes of the rib cage widths are displayed as the feature quantities indicating the motion of the entire lung field; however, the waveforms to be displayed are not limited to these. For example, a waveform showing a time change of the average signal value of the entire lung field or waveforms showing time changes of the average signal values of the respective left and right lungs may be displayed as the feature quantity indicating the motion of the entire lung field. Moreover, the feature quantities to be displayed by the waveforms may be settable by the user through the operation unit 33.

Moreover, in the above-described embodiments, the description has been made on the assumption that the same types of feature quantities are calculated for the respective sub-regions; however, different feature quantities may be calculated for each of the sub-regions.

Moreover, for example, in the above description, there is disclosed an example of using a hard disk, a semiconductor non-volatile memory or the like as a computer-readable medium storing a program according to the present invention; however, a computer-readable medium according to the present invention is not limited to this example. As another computer-readable medium, a portable recording medium such as a CD-ROM is applicable. Moreover, as a medium that provides data of the programs according to the present invention through a communication line, a carrier wave is also applied.

In addition, the detailed configurations and detailed operations of the respective apparatuses configuring the diagnosis assistance system 100 are also appropriately changeable within the scope without departing from the spirit of the present invention.

Note that the entire contents of Japanese Patent Application No. 2010-190240 including the specification, the scope of claims, the drawings and the abstract, filed on Aug. 27, 2010, are directly incorporated in a part of this application.

Industrial Applicability

The present invention is applicable in the diagnosis of the chest movement in the medical field.

Description of Reference Numerals
100 DIAGNOSIS ASSISTANCE SYSTEM
1 IMAGING APPARATUS
11 RADIATION GENERATION DEVICE
111 RADIATION SOURCE
112 RADIATION SOURCE HOLDING PORTION
113 SUPPORT BASE SHAFT
12 RADIATION IRRADIATION CONTROL DEVICE
13 RADIATION DETECTION UNIT
131 RADIATION DETECTOR
132 DETECTOR HOLDING PORTION
133 SUPPORT BASE SHAFT
14 READING CONTROL DEVICE
2 IMAGING CONSOLE
21 CONTROL UNIT
22 STORAGE UNIT
23 OPERATION UNIT
24 DISPLAY UNIT
25 COMMUNICATION UNIT
26 BUS
3 DIAGNOSTIC CONSOLE
31 CONTROL UNIT
32 STORAGE UNIT
33 OPERATION UNIT
34 DISPLAY UNIT
35 COMMUNICATION UNIT
36 BUS

The invention claimed is:
1. A diagnosis assistance system for use with a lung field of a subject, the diagnosis assistance system comprising:
an imaging unit structured to perform dynamic imaging of the lung field and generate a plurality of successive image frames;
a first analysis unit structured to extract a lung field region from each of the plurality of generated image frames, divide the extracted lung field region into a plurality of regions, and analyze the divided regions correlated among the plurality of image frames, thereby calculating a feature quantity indicating motions of the divided regions;
a second analysis unit structured to calculate a feature quantity indicating a motion of the entire lung field region based on at least one of movement of a rib, a diaphragm, a collarbone or a shoulder of the lung field region; and a display unit structured to simultaneously display the feature quantity, the feature quantity being calculated by the first analysis unit and the second analysis unit.

2. The diagnosis assistance system of claim 1, wherein the second analysis unit is structured to calculate the feature quantity indicating a restriction degree of chest breathing and a restriction degree of a motion of a rib cage based on the movement of the rib or the diaphragm.

3. The diagnosis assistance system of claim 1, wherein the second analysis unit is structured to calculate the feature quantity indicating a restriction degree of a motion of an accessory respiratory muscle based on the movement of the collarbone or the shoulder.

4. The diagnosis assistance system of claim 1, wherein the feature quantity indicating the motion of the divided region is a feature quantity indicating ventilation or blood flow of the region.

5. The diagnosis assistance system of claim 1, further comprising:

an operation unit structured to allow a user to select a region serving as a display target of an analysis result by the first analysis unit, wherein the first analysis unit is structured to calculate the feature quantity indicating the motion of the region selected with the operation unit; and the display unit is structured to display the feature quantity indicating the motion of the selected region.

6. A diagnosis assistance system for use with a subject, the diagnosis assistance system comprising:

an imaging unit structured to perform dynamic imaging of the subject and which generates a plurality of successive image frames;

an analysis unit structured to extract a subject region from each of the plurality of generated image frames, structured to divide the extracted subject region into a plurality of regions, and structured to analyze the divided regions correlated among the plurality of image frames, thereby calculating a predetermined feature quantity indicating motions of the divided regions;

an operation unit structured to allow a user to select a region serving as a display target of an analysis result by the analysis unit from among the divided regions; and a display unit structured to display the feature quantity regarding the region selected by the operation unit, the feature quantity being calculated by the analysis unit;

wherein the analysis unit calculates an average value of pixel signal values in the divided region of the plurality of image frames, and calculates a time change of a calculated average signal value as a feature quantity indicating a motion of the region, and the display unit displays, as a waveform, the time change of the average signal value of the region selected by the operation unit, the time change being calculated by the analysis unit.

7. A diagnosis assistance system for use with a subject, the diagnosis assistance system comprising:

an imaging unit structured to perform dynamic imaging of the subject and which generates a plurality of successive image frames;

an analysis unit structured to extract a subject region from each of the plurality of generated image frames, structured to divide the extracted subject region into a plurality of regions, and structured to analyze the divided regions correlated among the plurality of image frames, thereby calculating a predetermined feature quantity indicating motions of the divided regions;

an operation unit structured to allow a user to select a region serving as a display target of an analysis result by the analysis unit from among the divided regions; and a display unit structured to display the feature quantity regarding the region selected by the operation unit, the feature quantity being calculated by the analysis unit;

wherein the imaging unit is a unit for imaging a dynamic image of a chest portion, and in a case where one region of lung field regions is selected by the operation unit, the display unit displays a feature quantity of a region of other lung field that is body axis-symmetric to the selected region simultaneously with a feature quantity of the selected region.

\* \* \* \* \*